(12) United States Patent  
Conquergood et al.

(10) Patent No.: US 8,201,563 B2  
(45) Date of Patent: Jun. 19, 2012

(54) METHOD FOR INTRODUCING MATERIALS INTO A BODY

(75) Inventors: Laura Conquergood, Mississauga (CA); Mark Leung, Toronto (CA); Caitlyn Paget, Toronto (CA)

(73) Assignee: Kimberly-Clark, Inc. (CA)

(*) Notice: Subject to any disclaimer, the term of this patent is extended or adjusted under 35 U.S.C. 154(b) by 1756 days.

(21) Appl. No.: 11/368,508

(22) Filed: Mar. 7, 2006

(65) Prior Publication Data

US 2006/0206131 A1    Sep. 14, 2006

Related U.S. Application Data

(63) Continuation-in-part of application No. 11/128,342, filed on May 13, 2005, now Pat. No. 8,043,287.

(60) Provisional application No. 60/594,109, filed on Mar. 11, 2005.

(51) Int. Cl.  
*A61B 17/32* (2006.01)

(52) U.S. Cl. ............... 128/898; 606/20; 606/31; 606/41; 606/45; 606/49; 606/170; 606/180; 607/96; 607/101

(58) Field of Classification Search ............... 606/20–31, 606/41, 47, 49; 607/96, 101; 128/898  
See application file for complete search history.

(56) References Cited

U.S. PATENT DOCUMENTS

| | | | |
|---|---|---|---|
| 2,526,662 A | 10/1950 | Hipps et al. | |
| 3,477,423 A | 11/1969 | Griffith | |
| 3,732,858 A | 5/1973 | Banko | |
| 3,774,612 A * | 11/1973 | Marco | 604/275 |
| 4,177,797 A | 12/1979 | Baylis et al. | |
| 4,369,788 A | 1/1983 | Goald | |
| 4,411,266 A | 10/1983 | Cosman | |
| 4,512,344 A | 4/1985 | Barber | |
| 4,600,014 A | 7/1986 | Beraha | |
| 4,649,919 A | 3/1987 | Thimsen et al. | |
| 4,699,154 A | 10/1987 | Lindgren | |
| 4,834,729 A | 5/1989 | Sjostrom | |
| 4,857,046 A | 8/1989 | Stevens et al. | |
| 4,883,458 A | 11/1989 | Shiber | |
| 4,907,589 A | 3/1990 | Cosman | |
| 4,958,625 A | 9/1990 | Bates et al. | |

(Continued)

FOREIGN PATENT DOCUMENTS

EP    0438242    7/1991

(Continued)

OTHER PUBLICATIONS

International Search Report for PCT Application No. PCT/CA2006/000349 (Filed on Mar. 10, 2006), Mailed on Jun. 29, 2006.

(Continued)

*Primary Examiner* — Aaron Roane  
(74) *Attorney, Agent, or Firm* — Dority & Manning, P.A.

(57) ABSTRACT

The invention comprises a method for introduction of materials into a patient's body. The method generally comprises providing an elongate member for introducing the material. The elongate member defines a lumen and comprises a distal end defining an aperture and a proximal end. The method further comprises the steps of positioning the elongate member at a target site of a patient's body; providing a motorized device at least partially disposed within the lumen; and introducing the material through the lumen into the target site using the motorized device.

18 Claims, 13 Drawing Sheets

U.S. PATENT DOCUMENTS

| | | |
|---|---|---|
| 4,979,939 A | 12/1990 | Shiber |
| 5,002,553 A | 3/1991 | Lein et al. |
| 5,027,792 A | 7/1991 | Meyer |
| 5,074,841 A | 12/1991 | Ademovic et al. |
| 5,084,052 A | 1/1992 | Jacobs |
| RE34,056 E | 9/1992 | Lindgren et al. |
| 5,167,658 A | 12/1992 | Ensslin |
| 5,183,054 A | 2/1993 | Burkholder et al. |
| 5,201,729 A | 4/1993 | Hertzmann et al. |
| 5,233,515 A | 8/1993 | Cosman |
| 5,234,000 A | 8/1993 | Hakky et al. |
| 5,277,201 A | 1/1994 | Stern |
| 5,334,193 A | 8/1994 | Nardella |
| 5,342,357 A | 8/1994 | Nardella |
| 5,383,874 A | 1/1995 | Jackson et al. |
| 5,383,884 A * | 1/1995 | Summers ............ 606/170 |
| 5,423,799 A | 6/1995 | Shiu |
| 5,423,807 A | 6/1995 | Milder |
| 5,423,811 A | 6/1995 | Imran et al. |
| 5,433,739 A | 7/1995 | Sluijter et al. |
| 5,437,662 A | 8/1995 | Nardella |
| 5,458,596 A | 10/1995 | Lax et al. |
| 5,484,400 A | 1/1996 | Edwards et al. |
| 5,486,161 A | 1/1996 | Lax et al. |
| 5,520,682 A | 5/1996 | Baust et al. |
| 5,536,267 A | 7/1996 | Edwards et al. |
| 5,546,161 A | 8/1996 | Sakai et al. |
| 5,569,242 A | 10/1996 | Lax et al. |
| 5,569,284 A * | 10/1996 | Young et al. ............ 606/180 |
| 5,571,147 A | 11/1996 | Sluijter et al. |
| 5,574,117 A | 11/1996 | Yoshida et al. |
| 5,591,187 A | 1/1997 | Dekel |
| 5,599,346 A | 2/1997 | Edwards et al. |
| 5,603,221 A | 2/1997 | Maytal |
| 5,647,871 A | 7/1997 | Levine et al. |
| 5,651,780 A | 7/1997 | Jackson et al. |
| 5,658,278 A | 8/1997 | Imran et al. |
| 5,688,267 A | 11/1997 | Panescu et al. |
| 5,697,927 A | 12/1997 | Imran et al. |
| 5,718,701 A | 2/1998 | Shai et al. |
| 5,735,847 A | 4/1998 | Gough et al. |
| 5,785,705 A | 7/1998 | Baker |
| 5,800,481 A | 9/1998 | Loos |
| 5,810,804 A | 9/1998 | Bough et al. |
| 5,873,882 A | 2/1999 | Straub et al. |
| 5,876,414 A | 3/1999 | Straub |
| 5,906,612 A | 5/1999 | Chinn |
| 5,913,859 A | 6/1999 | Shapira |
| 5,916,163 A | 6/1999 | Panescu et al. |
| 5,928,159 A | 7/1999 | Eggers et al. |
| 5,957,922 A | 9/1999 | Imran |
| 5,957,961 A | 9/1999 | Maguire et al. |
| 5,968,062 A | 10/1999 | Thomas et al. |
| 5,971,980 A | 10/1999 | Sherman |
| 5,980,504 A | 11/1999 | Sharkey et al. |
| 5,983,141 A | 11/1999 | Sluijter et al. |
| 6,007,570 A * | 12/1999 | Sharkey et al. ............ 607/96 |
| 6,015,407 A | 1/2000 | Rieb et al. |
| 6,016,809 A | 1/2000 | Mulier et al. |
| 6,024,751 A | 2/2000 | Lovato et al. |
| 6,032,673 A * | 3/2000 | Savage et al. ............ 128/898 |
| 6,033,399 A | 3/2000 | Gines |
| 6,035,238 A | 3/2000 | Ingle et al. |
| 6,051,019 A | 4/2000 | Dobak, III |
| 6,053,912 A | 4/2000 | Panescu et al. |
| 6,053,937 A | 4/2000 | Edwards et al. |
| 6,063,085 A | 5/2000 | Tay et al. |
| 6,073,051 A | 6/2000 | Sharkey et al. |
| 6,074,386 A | 6/2000 | Goble et al. |
| 6,074,389 A | 6/2000 | Levine et al. |
| 6,074,412 A | 6/2000 | Mikus et al. |
| 6,083,237 A | 7/2000 | Huitema et al. |
| 6,095,149 A | 8/2000 | Sharkey et al. |
| 6,099,514 A | 8/2000 | Sharkey et al. |
| 6,109,268 A | 8/2000 | Thapliyal et al. |
| 6,113,595 A | 9/2000 | Muntetmann |
| 6,122,549 A | 9/2000 | Sharkey et al. |
| 6,123,702 A | 9/2000 | Swanson et al. |
| 6,126,682 A | 10/2000 | Sharkey et al. |
| 6,136,014 A * | 10/2000 | Sirimanne et al. ............ 606/185 |
| 6,139,545 A | 10/2000 | Utley et al. |
| 6,146,380 A | 11/2000 | Racz et al. |
| 6,161,048 A | 12/2000 | Sluijter et al. |
| 6,183,468 B1 | 2/2001 | Swanson et al. |
| 6,197,021 B1 | 3/2001 | Panescu et al. |
| 6,206,876 B1 | 3/2001 | Levine et al. |
| 6,217,573 B1 | 4/2001 | Webster |
| 6,228,080 B1 | 5/2001 | Gines |
| 6,228,081 B1 | 5/2001 | Goble |
| 6,237,569 B1 | 5/2001 | Stelzer et al. |
| 6,238,387 B1 | 5/2001 | Miller, III |
| 6,241,725 B1 | 6/2001 | Cosman |
| 6,246,912 B1 | 6/2001 | Sluijter et al. |
| 6,258,086 B1 | 7/2001 | Ashley et al. |
| 6,259,952 B1 | 7/2001 | Sluijter et al. |
| 6,261,311 B1 | 7/2001 | Sharkey et al. |
| 6,264,650 B1 | 7/2001 | Hovda et al. |
| 6,264,651 B1 | 7/2001 | Underwood et al. |
| 6,273,861 B1 | 8/2001 | Bates et al. |
| 6,277,112 B1 | 8/2001 | Underwood et al. |
| 6,283,960 B1 | 9/2001 | Ashley |
| 6,283,961 B1 | 9/2001 | Underwood et al. |
| 6,290,715 B1 | 9/2001 | Sharkey et al. |
| 6,293,943 B1 | 9/2001 | Panescu et al. |
| 6,296,636 B1 | 10/2001 | Cheng et al. |
| 6,309,387 B1 | 10/2001 | Eggers et al. |
| 6,312,428 B1 | 11/2001 | Eggers et al. |
| 6,325,806 B1 | 12/2001 | Fox |
| 6,355,031 B1 | 3/2002 | Edwards et al. |
| 6,355,032 B1 | 3/2002 | Hovda et al. |
| 6,379,348 B1 | 4/2002 | Onik |
| 6,391,026 B1 | 5/2002 | Hung et al. |
| 6,416,508 B1 | 7/2002 | Eggers et al. |
| 6,432,103 B1 | 8/2002 | Ellsberry et al. |
| 6,451,015 B1 | 9/2002 | Rittman, III et al. |
| 6,461,353 B1 | 10/2002 | Baker, Jr. et al. |
| 6,464,695 B2 | 10/2002 | Hovda et al. |
| 6,468,270 B1 | 10/2002 | Hovda et al. |
| 6,468,274 B1 | 10/2002 | Alleyne et al. |
| 6,478,793 B1 | 11/2002 | Cosman et al. |
| 6,482,204 B1 | 11/2002 | Lax et al. |
| 6,491,690 B1 | 12/2002 | Goble et al. |
| 6,494,880 B1 | 12/2002 | Swanson et al. |
| 6,500,172 B1 | 12/2002 | Panescu et al. |
| 6,500,173 B2 | 12/2002 | Underwood et al. |
| 6,506,189 B1 | 1/2003 | Rittman, III et al. |
| 6,517,568 B1 | 2/2003 | Sharkey et al. |
| 6,530,992 B1 | 3/2003 | Yank et al. |
| 6,533,780 B1 | 3/2003 | Laird et al. |
| 6,540,741 B1 | 4/2003 | Underwood et al. |
| 6,544,195 B2 | 4/2003 | Wilson et al. |
| 6,547,810 B1 | 4/2003 | Sharkey et al. |
| 6,557,559 B1 | 5/2003 | Eggers et al. |
| 6,558,381 B2 | 5/2003 | Ingle et al. |
| 6,575,968 B1 | 6/2003 | Eggers et al. |
| 6,575,969 B1 | 6/2003 | Rittman, Jr. et al. |
| 6,584,360 B2 | 6/2003 | Francischelli et al. |
| 6,587,731 B1 | 7/2003 | Ingle et al. |
| 6,602,248 B1 | 8/2003 | Sharps et al. |
| 6,604,003 B2 | 8/2003 | Fredricks et al. |
| 6,613,047 B2 | 9/2003 | Edwards |
| 6,620,155 B2 | 9/2003 | Underwood et al. |
| 6,645,203 B2 | 11/2003 | Sharkey et al. |
| 6,645,464 B1 | 11/2003 | Hainfeld |
| 6,652,513 B2 | 11/2003 | Panescu et al. |
| 6,673,023 B2 | 1/2004 | Pfluegger |
| 6,673,063 B2 | 1/2004 | Brett |
| 6,702,810 B2 | 3/2004 | McClurken et al. |
| 6,706,038 B2 | 3/2004 | Francischelli et al. |
| 6,712,811 B2 | 3/2004 | Underwood et al. |
| 6,712,813 B2 | 3/2004 | Ellman et al. |
| 6,712,816 B2 | 3/2004 | Hung et al. |
| 6,723,091 B2 | 4/2004 | Goble et al. |
| 6,726,684 B1 | 4/2004 | Woloszko et al. |
| 6,726,685 B2 | 4/2004 | To et al. |
| 6,730,081 B1 | 5/2004 | Desai |
| 6,733,496 B2 | 5/2004 | Ashley et al. |

| | | | |
|---|---|---|---|
| 6,736,815 B2 | 5/2004 | Ginn | |
| 6,749,605 B2 | 6/2004 | Ashley et al. | |
| 6,749,617 B1 | 6/2004 | Palasis et al. | |
| 6,767,347 B2 | 7/2004 | Sharkey et al. | |
| 6,772,012 B2 | 8/2004 | Ricart et al. | |
| 6,783,532 B2 | 8/2004 | Steiner et al. | |
| 6,796,982 B2 | 9/2004 | Carmet et al. | |
| 6,821,276 B2 | 11/2004 | Lambrecht et al. | |
| 6,827,716 B2 | 12/2004 | Ryan et al. | |
| 6,832,996 B2 | 12/2004 | Woloszko et al. | |
| 6,832,997 B2 | 12/2004 | Uchida et al. | |
| 6,837,884 B2 | 1/2005 | Woloszko | |
| 6,837,888 B2 | 1/2005 | Ciarrocca et al. | |
| 6,846,314 B2 | 1/2005 | Shapira | |
| 6,878,155 B2 | 4/2005 | Sharkey et al. | |
| 6,896,675 B2 | 5/2005 | Leung et al. | |
| 6,929,640 B1 | 8/2005 | Underwood et al. | |
| 6,997,941 B2 | 2/2006 | Sharkey et al. | |
| 7,097,641 B1 | 8/2006 | Arless et al. | |
| 7,267,683 B2 | 9/2007 | Sharkey et al. | |
| 7,282,061 B2 | 10/2007 | Sharkey et al. | |
| 7,309,336 B2 | 12/2007 | Ashley et al. | |
| 7,400,930 B2 | 7/2008 | Sharkey et al. | |
| 7,593,778 B2 | 9/2009 | Chandran et al. | |
| 2001/0001314 A1 | 5/2001 | Davison et al. | |
| 2001/0025176 A1 | 9/2001 | Ellsberry et al. | |
| 2001/0025177 A1 | 9/2001 | Eoloszko et al. | |
| 2001/0032002 A1 | 10/2001 | McClurken et al. | |
| 2002/0019626 A1* | 2/2002 | Sharkey et al. | 606/15 |
| 2002/0032441 A1 | 3/2002 | Ingle et al. | |
| 2002/0072688 A1 | 6/2002 | Burbank et al. | |
| 2002/0128641 A1 | 9/2002 | Underwood et al. | |
| 2002/0138020 A1 | 9/2002 | Pflueger | |
| 2002/0138091 A1 | 9/2002 | Pflueger | |
| 2002/0188290 A1 | 12/2002 | Sharkey et al. | |
| 2002/0188292 A1 | 12/2002 | Sharkey et al. | |
| 2002/0193790 A1 | 12/2002 | Fleischman et al. | |
| 2003/0158545 A1 | 8/2003 | Hovda et al. | |
| 2004/0002746 A1 | 1/2004 | Ryan et al. | |
| 2004/0059254 A1 | 3/2004 | Pflueger | |
| 2004/0064137 A1 | 4/2004 | Pellegrino et al. | |
| 2004/0176759 A1 | 9/2004 | Krishnamurthy et al. | |
| 2004/0193151 A1 | 9/2004 | To et al. | |
| 2004/0215181 A1 | 10/2004 | Christopherson et al. | |
| 2005/0177209 A1 | 8/2005 | Leung et al. | |
| 2005/0209530 A1 | 9/2005 | Pflueger | |
| 2005/0234445 A1 | 10/2005 | Conquergood et al. | |

FOREIGN PATENT DOCUMENTS

| | | |
|---|---|---|
| EP | 966920 | 12/1999 |
| EP | 966920 A2 | 12/1999 |
| EP | 1059067 | 12/2000 |
| EP | 1402838 | 3/2004 |
| IT | 1246197 | 11/1994 |
| WO | WO 98/17190 | 4/1998 |
| WO | WO 99/47058 | 9/1999 |
| WO | WO 01/45579 | 6/2001 |
| WO | WO 01/57655 | 8/2001 |
| WO | WO 01/62168 | 8/2001 |
| WO | WO 01/74251 | 10/2001 |
| WO | WO 03/073948 | 9/2003 |
| WO | WO 2005/110263 | 11/2005 |

OTHER PUBLICATIONS

Choy et al., "B. Fall of Intradiscal Pressure with Laser Ablation", J. Clin. Laser Med. & Surg., vol. 13, No. 3, 1995, Mary Ann Liebert, Inc., pp. 149-151.

Case et al., "Changes of Intradisc Pressure Versus Volume Change", J. Clin. Laser Med. Surg., Jun. 1995, vol. 13(3), pp. .143-147.

Cripton et al., "A minimally disruptive technique for measuring intervertebral disc pressure in vitro: application to the cervical spine", J. Biomech, Apr. 2001, vol. 34(4), 545-549.

Wilke et al., "New in vivo measurements of pressures in the intervertebral disc in daily life", Spine, Apr. 1999, vol. 15:24(8), pp. 755-762.

McNally et al., "Development and validation of a new transducer for intradiscal pressure measurement", J. Biomed. Eng., Nov. 1992, vol. 14(6), pp. 495-498.

Panjabi et al., "Intrinsic Disc Pressure as a Measurement of Integrity of the Lumbar Spine", Spine, Aug. 1988, vol. 13(8), pp. 913-977.

Amorettia et al., "Preliminary communication on a decompression probe (Dekompressor1) in percutaneous discectomy. Ten case reports". Journal of Clinical Imaging 29 (2005) 98-101.

Amorettia et al., "Preliminary Communication on a Decompression Probe (Dekompressor1) in Percutaneous Discectomy. Ten Case Reports", Journal of Clinical Imaging 29 (2005) 98-101.

Case et al., "Changes of Intradisc Pressure Versus Volume Change", J. Clin. Laser Med & Surg., Jun. 1995, vol. 13(3), pp. 143-147.

Choy et al., "B. Fall of Intradiscal Pressure with Laser Ablation", J. Clin. Laser Med & Surg., vol. 13, No. 3, 1995, pp. 149-151.

Cripton et al., "A Minimally Disruptive Technique for Measuring Intervertebral Disc Pressure in Vitro: Application to the Cervical Spine", J. Biomech, Apr. 2001, vol. 34 (4), 545-549.

McNally et al., "Development and Validation of a New Transducer for Intradiscal Pressure Measurement", J. Biomed. Eng., Nov. 1992, vol. 14(6) 495-498.

Panjabi et al., "Intrinsic Disc Pressure as a Measurement of Integrity of the Lumbar Spine", Spine, Aug. 1988, vol. 13(8) 913-977.

Wilke et al., "New in Vivo Measurements of Pressure in the Intervertebral Disc in Daily Life", Spine, Apr. 1999, vol. 15:24(8), 913-977.

* cited by examiner

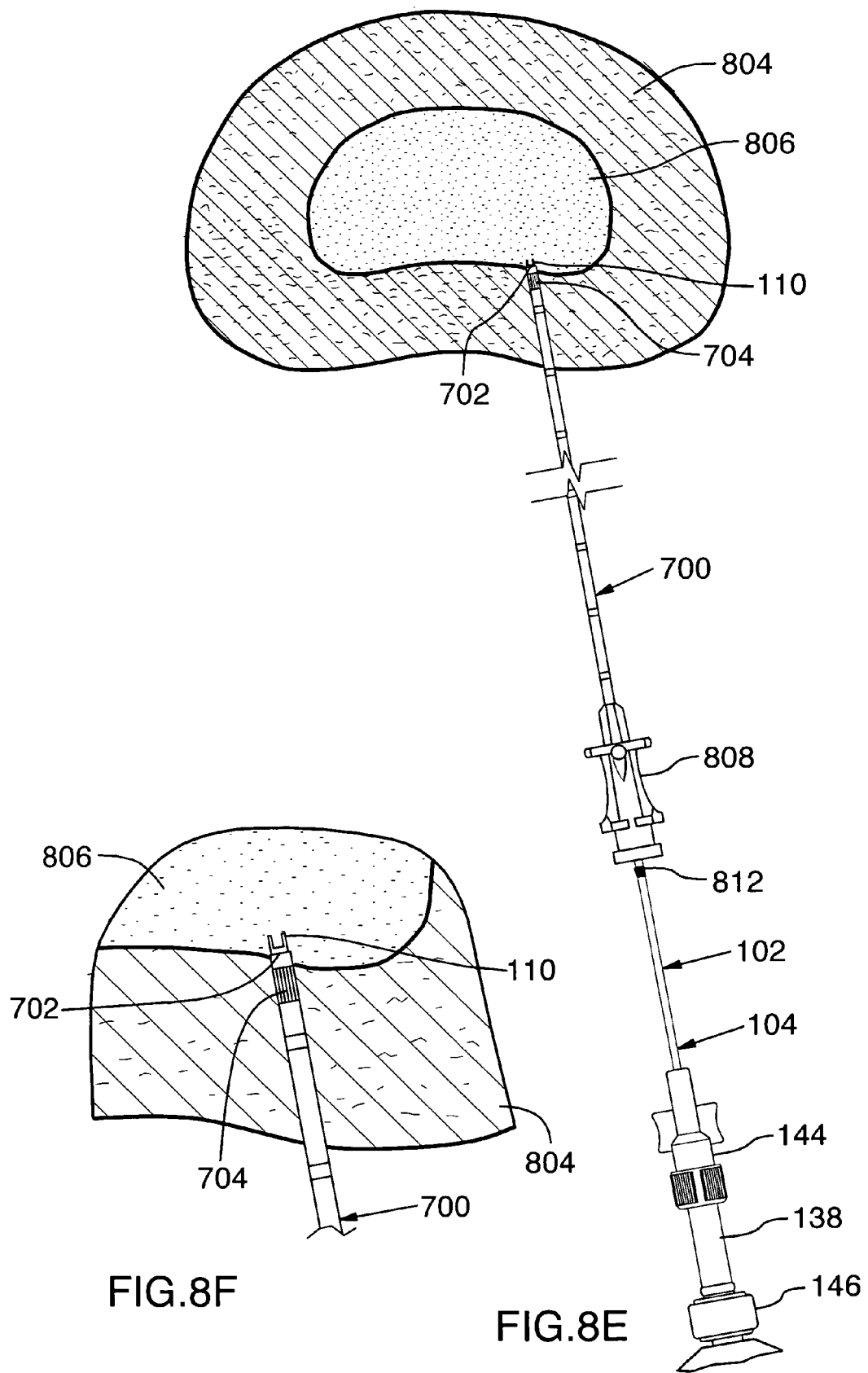

METHOD FOR INTRODUCING MATERIALS INTO A BODY

TECHNICAL FIELD

This application claims priority from and is a continuation-in-part of co-pending U.S. patent application Ser. No. 11/128,342, filed May 13, 2005. In addition, this application claims the benefit of: U.S. provisional application No. 60/594,109 filed Mar. 1, 2005. The aforementioned applications are all herein incorporated by reference.

The invention relates to methods for introduction of materials into a patient's body. More particularly, the invention relates to such methods that are minimally invasive.

BACKGROUND OF THE ART

A number of medical conditions exist that may require exogenous materials to be introduced into a patient's body. For example, syringes are commonly used to inject fluids into a patient. Syringes however, may not be suitable for more viscous or fibrous materials, such as collagen. Furthermore, when the procedure requires that material be removed from the body in addition to the introduction of exogenous material, a syringe may not be suitable.

BRIEF DESCRIPTION OF THE DRAWINGS

In order that the invention may be readily understood, embodiments of the invention are illustrated by way of examples in the accompanying drawings, in which.

DETAILED DESCRIPTION OF THE INVENTION

Figure 1A:
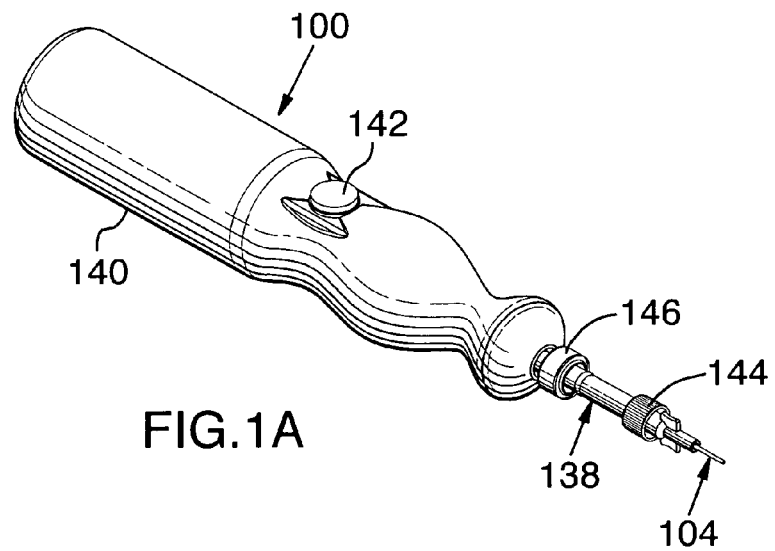
FIG. 1A is a perspective view of one embodiment of the device of the invention.

With specific reference now to the drawings in detail, it is stressed that the particulars shown are by way of example and for purposes of illustrative discussion of certain embodiments of the present invention only, and are presented in the cause of providing what is believed to be the most useful and readily understood description of the principles and conceptual aspects of the invention. In this regard, no attempt is made to show structural details of the invention in more detail than is necessary for a fundamental understanding of the invention, the description taken with the drawings making apparent to those skilled in the art how the several forms of the invention may be embodied in practice.

Before explaining at least one embodiment of the invention in detail, it is to be understood that the invention is not limited in its application to the details of construction and the arrangement of the components set forth in the following description or illustrated in the drawings. The invention is capable of other embodiments or of being practiced or carried out in various ways. Also, it is to be understood that the phraseology and terminology employed herein is for the purpose of description and should not be regarded as limiting.

DEFINITIONS

As used herein, the term "at", for example when referring to something being located "at" a specific location, is intended to include any one or more of: proximate, on, near, adjacent to or within the specific location.

As used herein, the terms "distal" and "proximal" are defined with respect to the user. In other words, the term "distal" refers to the part or portion further away from the user, while the term "proximal" refers to the part or portion closer to the user.

As used herein, the "posterior portion" of the nucleus pulposus refers to the approximately half of the nucleus pulposus that is closest to the dorsal side of the body, and the "anterior portion" of the nucleus pulposus refers to the approximately half of the nucleus pulposus that is closest to the ventral side of the body.

As used herein, the term "shaft" refers to an elongate element having either a closed or open distal end.

As used herein, the term "bent" refers to any deviation from a longitudinal axis.

As used herein, the term "slot" refers to an outcutting, slit, gap, or hole and is not limited in size or shape.

As used herein, the term "obturator" refers to any item that substantially fills or blocks a lumen.

As used herein, the term "cannula" is defined as an elongate device defining a lumen.

As used herein, the term "coring" refers to advancing an elongate member defining a lumen and having an open distal end into a tissue, wherein the advancement results in the incorporation or gathering of at least a portion of the tissue into the lumen of the elongate member.

As used herein, the phrase "operatively connected" is intended to mean "coupled or connected, either directly or indirectly, such that the connected structures are operable to perform a desired function".

As used herein, the term "conveyance" refers to facilitation of movement of a material from one location to another.

Finally, as used herein, the term "fully disposed" refers to a first member being substantially fully received within a second member such that, under normal use, it is not intended to be inserted into the other member any further.

Device

In one broad aspect, the present invention comprises an apparatus for removal of materials from the body of a patient. In one specific embodiment of the method, the apparatus is used for removal of nucleus pulposus tissue from an intervertebral disc. The apparatus may generally comprise a tissue removal member housed at least partially within an elongate member defining a lumen, for example a sheath. The tissue removal member may be any device that functions to convey tissue from the distal end of the elongate member to a portion exterior to the patient's body. In one embodiment, the tissue removal member is a shaft with at least one projection extending outwardly from the shaft. The shaft may have a plurality of projections extending outwardly therefrom. In one embodiment, the tissue removal member is operatively connected to a motor or other source of rotational energy which provides the motion required to remove the tissue.

Figure 1B:
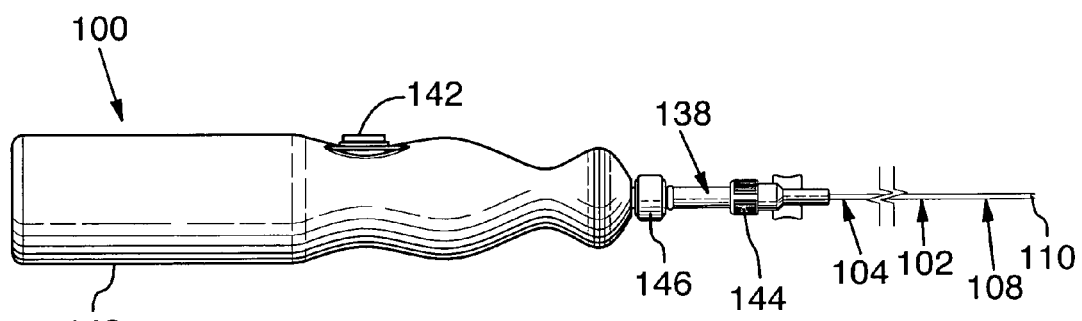
FIG. 1B is a side-view of one embodiment of the device of the invention.
Figure 1C:
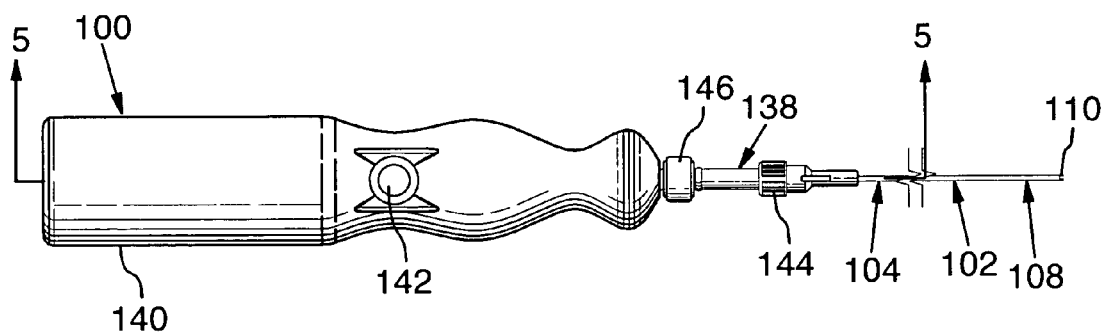
FIG. 1C is a top-view of one embodiment of the device of the invention.
Figure 2A:
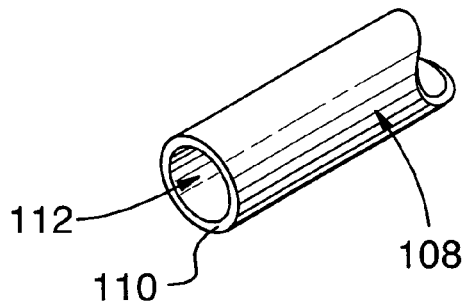
FIGS. 2A-D are perspective views of several embodiments of the distal portion of the elongate member.
Figure 2B:
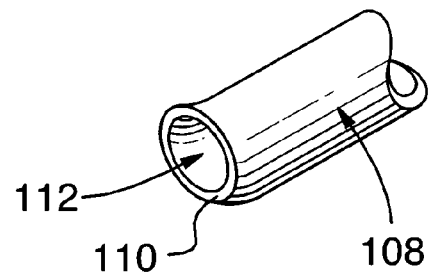
Figure 2C:
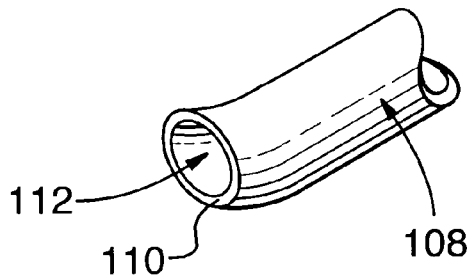
Figure 2D:
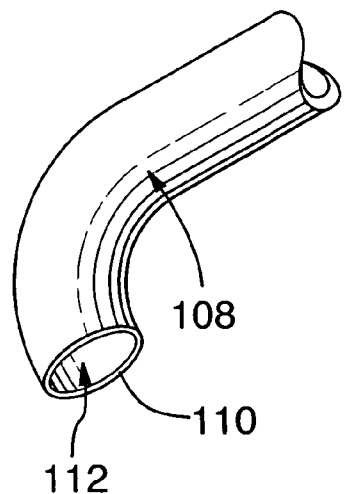

In the general embodiment shown in FIG. 1, the apparatus comprises an elongate member 102, a handpiece 140, and a receptacle 138 for collection or visualization of tissue.

In one embodiment of the present invention, elongate member 102 comprises proximal portion 104 ending in open proximal end 106, and distal portion 108 ending in open distal end 110. In other embodiments, described in more detail below, proximal end 106 may be closed and proximal portion 104 may define one or more apertures in a lateral wall thereof. Open distal end 110 defines aperture 112. In one specific embodiment, the cross-sectional shape of elongate member 102 is substantially circular, however alternate embodiments are possible, wherein the shape may be ovoid, square, or rectangular, and elongate member 102 is not limited in this regard. The plane in which aperture 112 is defined may be substantially perpendicular to the longitudinal axis of elongate member 102; however distal end 110 of elongate member 102 may be beveled or otherwise oriented, in which case the plane of aperture 112 would not necessarily be perpendicular to the longitudinal axis of the shaft.

In one specific embodiment, elongate member 102 is sized to be percutaneously directed to an interior tissue of the body. The length of elongate member 102 is generally between about 15.0 and about 25.0 cm, more specifically between about 17.0 and about 19.0 cm; however it may be otherwise sized to reach any target tissue within the body. The diameter of elongate member 102 is generally between about 0.5 and about 5.0 mm, more specifically between about 1.0 and about 2.0 mm, however it may be otherwise sized to fit within the space defined by the target tissue.

In one embodiment, elongate member 102 may be bent or curved, as shown in FIGS. 2A-2D. This may allow for easier access to a target site. The bend or curve may be applied by the user prior to or during the procedure, or may be applied during manufacture. Many angles are possible depending on the nature of the target tissue. For example, if the target tissue is the nucleus pulposus of an intervertebral disc, the curve may be at such an angle that the posterior portion of the nucleus pulposus may be reached with the device while allowing for an approach that reduces risk of damage to the spinal canal. In this example, the angle of curvature would generally be between about 1.0 and about 5.0°. Furthermore, the curve or bend may be located at various points along the length of the elongate member. Distal end 110 of elongate member 102 may additionally comprise a variety of geometries such as blunt, sharp, beveled, crown-shaped, fishhook shaped, or any other shape that will not interfere with the proper functioning of apparatus 100.

Elongate member 102 may be manufactured from a number of different materials. These include, but are not limited to, stainless steels, shape-memory materials such as nickel titanium alloys, polyesters, polyethylenes, polyurethanes, polyimides, nylons, copolymers thereof, and medical grade plastics. In one specific embodiment, elongate member 102 is made from a clear, transparent or translucent plastic or other material. This embodiment may allow the user to visualize the contents of elongate member 102 to ensure that it is operating properly.

In one embodiment, elongate member 102 is structured to define at least one slot in distal portion 108. The at least one slot 114 may function to allow more tissue to enter elongate member 102, and may allow for ease of movement through the target tissue, while still maintaining the separation of the non-target tissues from tissue removal member 116. Referring now to FIG. 4, slot(s) 114 may extend proximally from distal end 110 of elongate member 102. Slot(s) 114 may extend to a point on elongate member 102 that is substantially coplanar with distal end 136 of shaft 128 when shaft 128 is fully inserted into sheath 102. As used herein, the term 'substantially coplanar' may include any deviation from coplanarity that would not interfere with the functioning of the apparatus. Therefore, slot(s) 114 may extend to a point that is either proximal or distal to distal end 136 of shaft 128. In one embodiment, slot(s) 114 may be between about 0.5 mm and about 3 mm in length. Referring now to FIGS. 4A-4E, slot(s) 114 may be defined in a variety of shapes including rectangular, square, triangular, or any other shape that would not interfere with the proper functioning of apparatus 100. When a plurality of slots is included, the slots may be circumferentially arranged in any manner that will not interfere with the proper functioning apparatus 100. For example, elongate member 102 may include 2 slots that are diametrically opposite each other, or substantially adjacent to each other. In another example, elongate member 102 may include 3 slots that are equidistant from each other, or that are all arranged on one hemisphere of the distal end of the elongate member. In other embodiments, different arrangements and shapes of slots may be included. Furthermore, when a plurality of slots is included, the shape, positioning, or size of each of the slots need not be identical.

Slot(s) 114 may be created in a number of ways. For example, a Dremel or other rotary tool may be used to cut or sand slot 114 into elongate member 102. Alternatively, sheath 102 may be manufactured with slots 114 included.

Figure 3A:
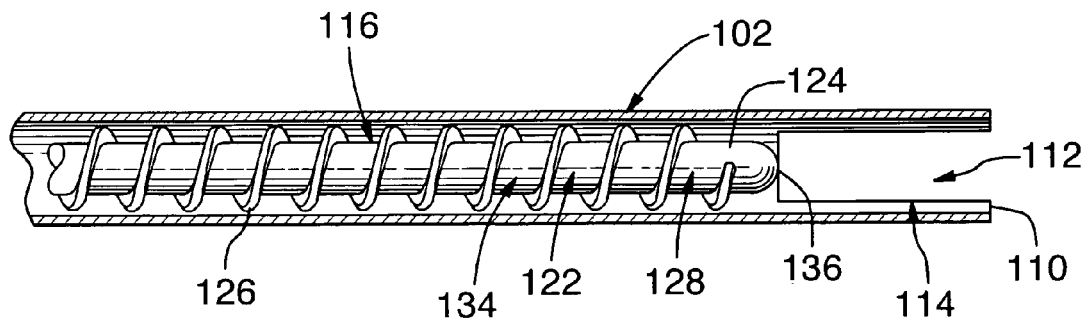
FIG. 3 is a sectional view of the distal portion of one embodiment of the apparatus.
Figure 5:
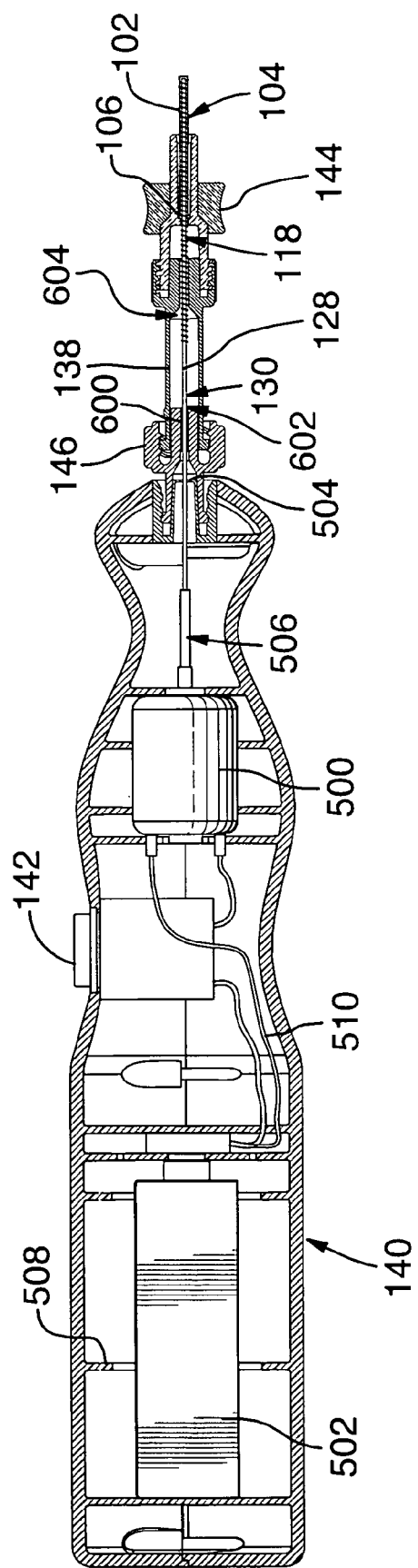
FIG. 5 is a sectional view of one embodiment of the apparatus.
Figure 7:
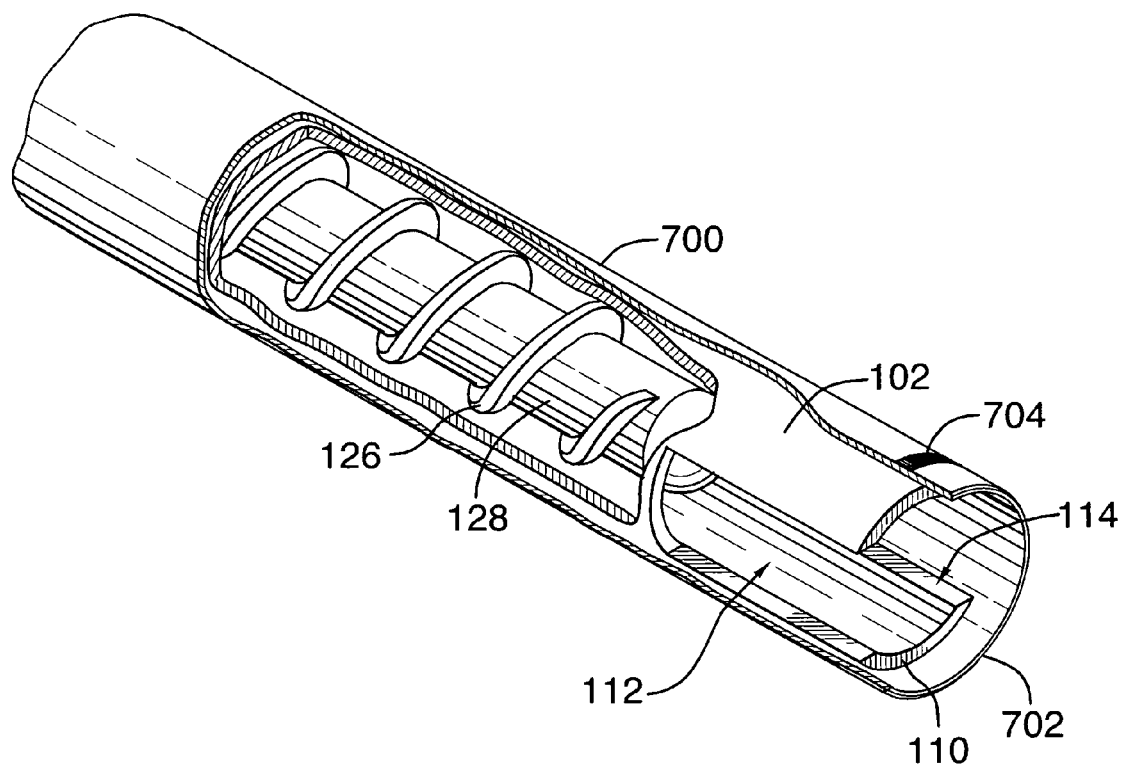
FIG. 7 is a cutaway view of the distal portion of one embodiment of the distal portion of the apparatus.

With respect to FIGS. 3, 5, and 7, apparatus 100 comprises tissue removal member 116, which is structured to be disposed within elongate member 102. Tissue removal member 116 comprises a proximal portion ending in a proximal end, and distal portion 122 ending in distal end 124. In one embodiment, tissue removal member 116 may be coaxial with elongate member 102; however tissue removal member 116 may be otherwise aligned. In one embodiment, the length of tissue removal member 116 is such that the proximal portion of tissue removal member 116 extends proximally beyond proximal end 106 of elongate member 102; however proximal ends of elongate member 102 and tissue removal member 116 may be flush or otherwise aligned. In a specific embodiment, distal end 124 of tissue removal member 116 is recessed proximally from the distal end of elongate member 102. This structure allows for distal portion 122 of tissue removal member 116 to be substantially shrouded within elongate member 102. This arrangement may protect surrounding tissues from being damaged by contact with tissue removal member 116. The distance by which tissue removal member 116 is recessed from distal end 110 of elongate member 102 is generally between about 0.5 and about 4.0 mm, more specifically between about 0.5 and about 2.0 mm; however, in this embodiment, the distance may be any amount such that tissue removal member 116 does not contact tissue until after the tissue has already entered elongate member 102. Further details regarding the recession of tissue removal member 116 are discussed hereinbelow.

Figure 3B:
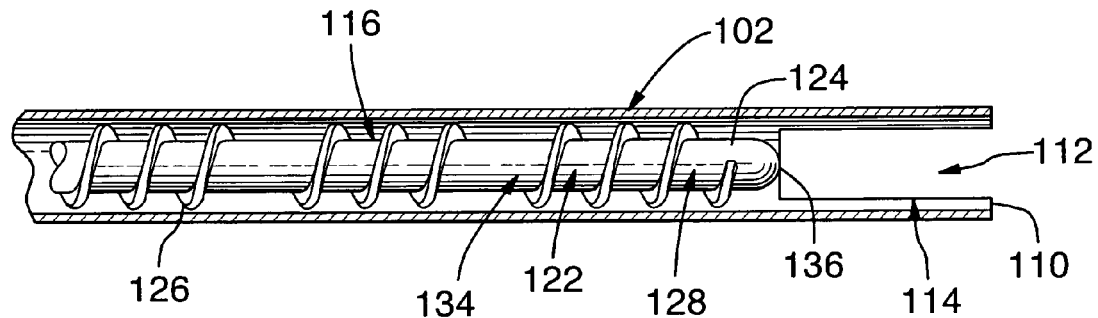
Figure 3C:
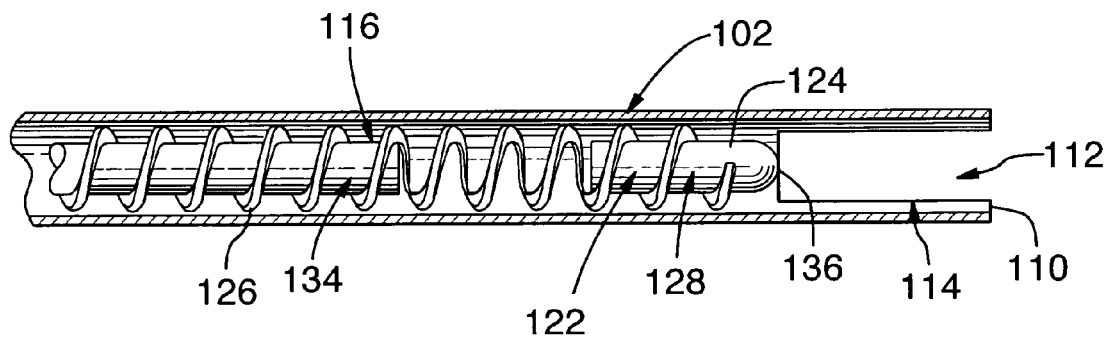
Figure 4A:
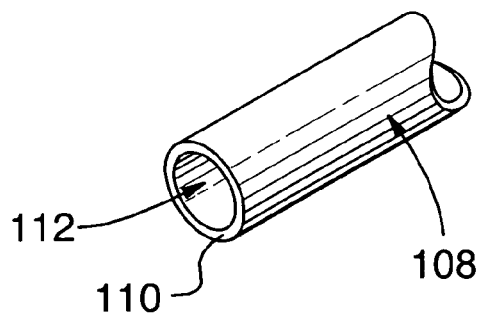
FIGS. 4A-E are perspective views of several embodiments of the slits of the apparatus.
Figure 4B:
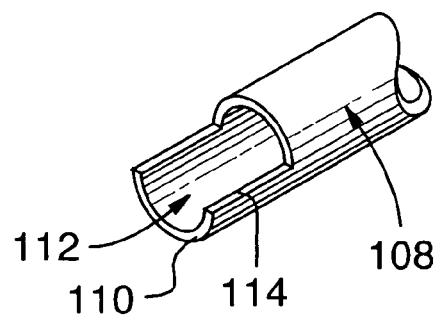
Figure 4C:
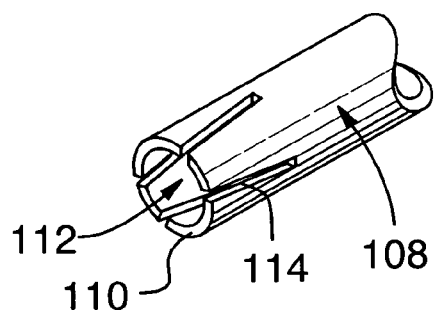
Figure 4D:
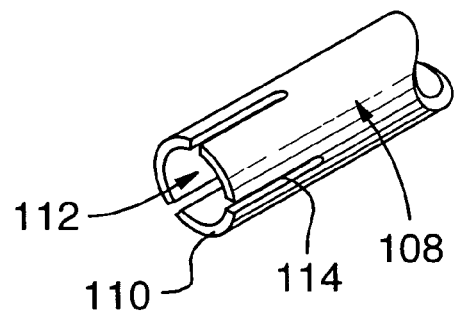
Figure 4E:
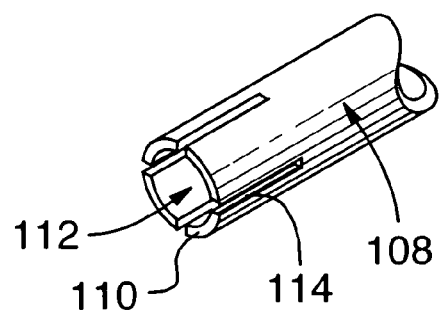

In one embodiment, tissue removal member 116 comprises a shaft 128 having outwardly extending projections 126. In a more specific embodiment, the outwardly extending projections may comprise a helical flighting or helical element disposed at least partially around shaft 128. This arrangement may functionally form an auger, wherein the term auger, refers to a device for moving or displacing material or liquid by means of a rotating helical flighting. However, any other structure that functions as an auger may be used, such as a screw or a drill bit. In one embodiment, outwardly extending projections 126 extend from distal portion 136 of shaft 128 and may end in proximal portion 130 of shaft 128. In a specific embodiment, outwardly extending projections 126 may end at a point located within receptacle 138, as described hereinbelow. Tissue removal member 116 is not limited to having one continuous helical projection; it may comprise a plurality of discrete projections that are either continuous or discontinuous over the length of the shaft, as shown in FIG. 3B. The geometry of the outwardly extending projections may vary in the thickness of the projections, the distance between projections, or in any other way that does not affect the functionality of the device. In addition, the diameter of projections 126 may be constant or may vary. In the case of a constant diameter, projections 126 may be sized such that tissue removal member 116 fits exactly within sheath 102, or projections 126 may be sized such that the diameter of tissue removal member 116 is smaller than the inner diameter of sheath 102. Furthermore, shaft 128 is not limited to one continuous shaft, and may comprise a plurality of shaft segments as shown in FIG. 3C.

Distal end 136 of shaft 128 of tissue removal member 116 may have many shapes, and the invention is not limited in this regard. For example, distal end 136 may be blunt, sharp, rounded, or otherwise shaped. Furthermore, distal portion 134 may be straight, bent, curved, beveled, or otherwise fashioned.

In one specific embodiment, outwardly extending projections 126 may be welded to shaft 128. In another embodiment, outwardly extending projections 126 may be integrally formed with shaft 128. Shaft 128 can be manufactured from a number of different materials. These include, but are not limited to, stainless steels, shape-memory materials such as nickel titanium alloys, polyesters, polyethylenes, polyurethanes, polyimides, nylons, copolymers thereof, and medical grade plastics. Furthermore, any combination of the above materials may be used to optimize the physical properties of apparatus 100. For example, a plastic coating disposed on a metal core may optimize flexibility and strength. Outwardly extending projections 126 may be manufactured from a number of different materials, including but not limited to stainless steels, nitinol, and various plastics and polymers. Outwardly extending projections 126 may be attached to shaft 128 by welding, for example laser welding, or by any other suitable method of joining two such components, such as crimping, soldering, or the use of adhesives. Alternatively, as mentioned above, projections 126 may be integrally formed with shaft 128 during the manufacturing process. In other words, shaft 128 and projections 126 may be manufactured or machined as one single device, such as the case of a screw or a drill-bit.

In one specific embodiment, shaft 128 may be at least partially coated with a substantially lubricious material. Such a material would be one that facilitates movement of shaft 128 through elongate member 102. In addition, the inner surface of elongate member 102 may be coated with such a material. Suitable lubricious materials include, but are not limited to, polytetrafluoroethylene, parylene, or tungstenite.

Tissue removal member 116 may generally be between about 6 inches and about 18 inches in length, more specifically between about 10.0 inches and about 13.5 inches. The diameter of shaft 128 may generally be between about 0.012 inches and about 0.042 inches, more specifically between about 0.016 inches and about 0.028 inches. The width of outwardly extending projections 126 may generally be between about 0.003 inches and about 0.025 inches, more specifically between about 0.005 inches and about 0.010 inches.

Figure 6:
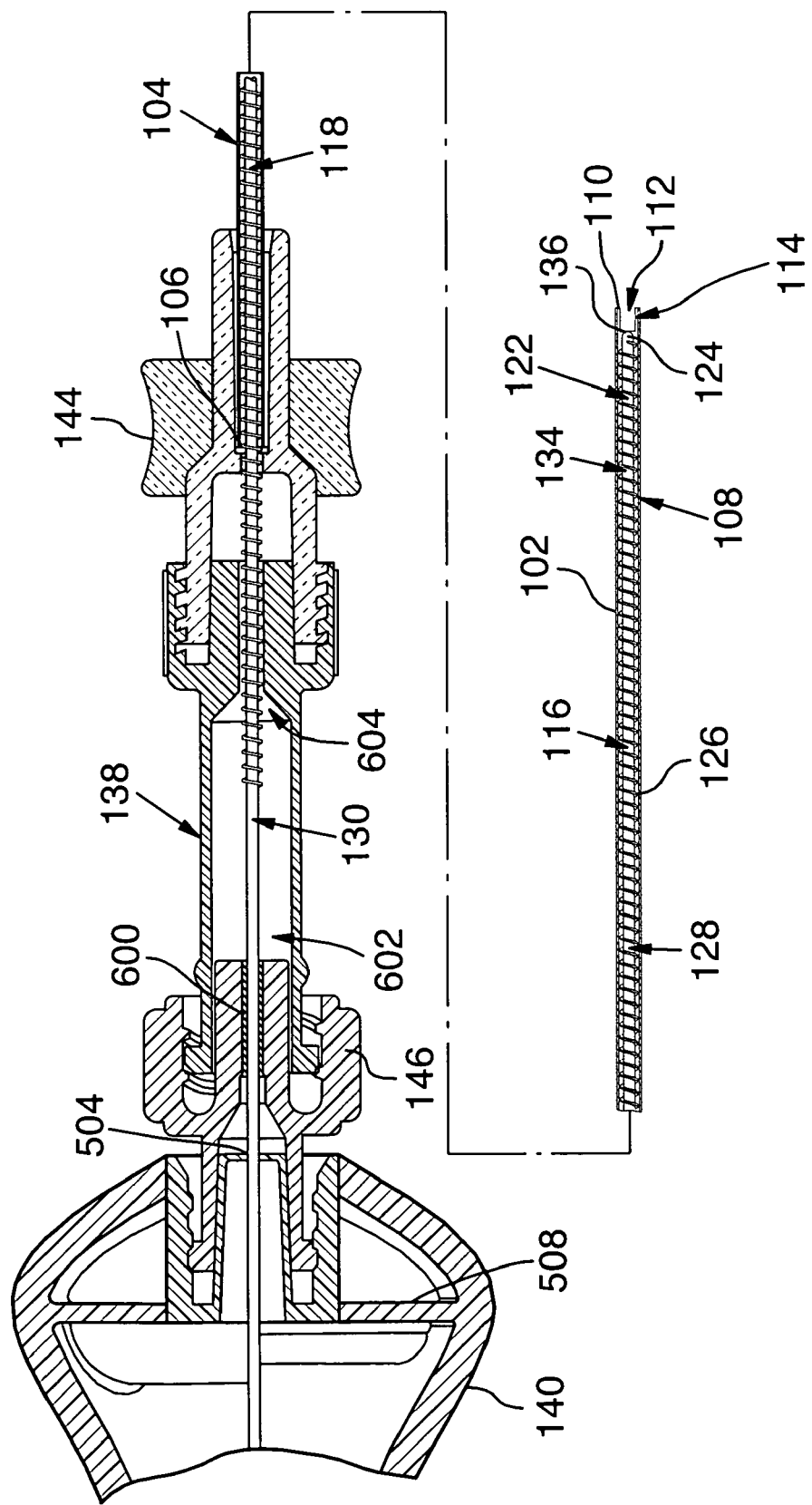
FIG. 6 is a sectional view of one embodiment of one portion of the apparatus.

As previously mentioned, apparatus 100 may comprise a receptacle for housing and/or viewing the tissue that is removed from the body. Herein, such a receptacle may be referred to as a collection chamber. Collection chamber 138 may be manufactured in a variety of sizes depending on the application. In one embodiment, collection chamber 138 may be structured to be coaxial with elongate member 102 and tissue removal member 116. In such an embodiment, collection chamber 138 may be located at, for example adjacent to, proximal portion 104 of elongate member 102, wherein proximal end 106 of elongate member 102 and distal portion 604 of collection chamber 138 are operatively connected, for example joined by a hub or lock 144. Hub or lock 144 may be a luer lock, snap fit, or any other type of hub or joining mechanism that does not interfere with the functioning of apparatus 100. In some embodiments, proximal portion 104 of elongate member 102 may define an opening such that tissue may exit therethrough and enter collection chamber 138. In the embodiment shown in FIG. 6, the opening is defined by proximal end 106 of elongate member 102. In other embodiments, proximal portion 104 of elongate member 102 may comprise one or more openings, for example in a lateral wall thereof, for allowing tissue to pass therethrough into collection chamber 138. It is to be noted that a means for tissue to exit proximal portion 104 of elongate member 102 is not limited to openings, and may include other means such as tubing, for example. In such embodiments, collection chamber 138 may be structured to receive tissue exiting proximal portion 104 of elongate member 102. For example, distal portion 604 of collection chamber 138 may define a hole or other opening that is aligned with open proximal end 106 of elongate member 102, such that tissue may exit elongate member 102 through open proximal end 106 and enter collection chamber 138 through the hole defined by distal portion 604. In some embodiments, tissue removal member 116 may extend through open proximal end 106 of elongate member 102 into, and optionally through, collection chamber 138, such that tissue may be deposited or viewed therein. In this embodiment, hub or lock 144 may be structured such that it does not interfere with the passage of tissue from elongate member 102 into collection chamber 138, and such that it allows tissue removal member 116 to extend from within the lumen of elongate member 102, through open proximal end 106, and into collection chamber 138. In a specific embodiment, outwardly extending projections 126 of tissue removal member 116 may end at a position within collection chamber 138. This may help to ensure that the tissue is deposited within collection chamber 138. Shaft 128 of tissue removal member 116 may further extend through proximal portion 602 of collection chamber 138. In some embodiments, collection chamber may be structured to be coupled to handpiece 140. In these embodiments, proximal portion 602 of collection chamber 138 may be joined to the distalmost portion of handpiece 140 with hub or lock 146. Hub or lock 146 may be a luer lock, snap fit, or any other hub or mechanism of joining that does not interfere with the functioning of apparatus 100. In a further embodiment, the collection chamber assembly may comprise a gasket 600 or any other device that would prevent tissue from exiting proximal portion 602 of collection chamber 138. In the specific embodiment shown in FIG. 6, distal portion 604 of collection chamber 138 is operatively connected to elongate member 102, proximal portion 602 of collection chamber 138 is operatively connected to handpiece 140, and shaft 128 of tissue removal member 116 runs through collection chamber 138 and into handpiece 140. In yet another embodiment, collection chamber 138 may be located within handpiece 140.

In some embodiments, collection chamber 138 may be structured to allow the user to visualize the contents of the chamber. This may be accomplished by manufacturing collection chamber 138 from a material that is clear, translucent, transparent, or otherwise pervious to light. Such materials include, but are not limited to, polycarbonate, polyvinylchloride, and polypropylene. In another embodiment, collection chamber 138 may include means for measuring the amount of tissue that is contained therein. The means may comprise, but are not limited to, volume markings on the chamber, a movable indicator that may be displaced by the tissue, or an electrically conductive marker that may lead to auto-shutoff when a certain amount of tissue has been removed. Furthermore, the moveable indicator may be structured such that it can be preset by the user at a particular location, thus facilitating the removal of a particular predetermined amount of tissue.

In one embodiment, collection chamber 138 may be structured to be detached from apparatus 100 while still maintaining the tissue within collection chamber 138. This may be accomplished by unscrewing or otherwise detaching collection chamber 138 from handle 140 and elongate member 102, and sliding collection chamber 138 off of apparatus 100. Collection chamber 138 can then be capped or otherwise closed or sealed with a snap-on cap, screw-cap, or any other means of sealing or closing collection chamber 138. This embodiment may allow for the tissue to be sent for further analysis, for example to a pathology laboratory. Persons skilled in the art will recognize that in some cases, tissue may stick to shaft 128 of tissue removal member 116. In these cases, after collection chamber 138 has been removed from apparatus 100, the user may simply manually remove the tissue from apparatus 100, and place it in a separate vial for collection. Alternatively, shaft 128 may be structured to be removed from handpiece 140 such that tissue can be slid or pulled off the proximal end of shaft 128. In one specific embodiment, a non-stick coating, such as Teflon, may be included on the portion of the shaft that is within collection chamber 138 to prevent tissue from sticking.

In another embodiment, collection chamber 138 may comprise a removable collection vessel, sac, or pouch for ease of tissue removal. This would be particularly useful in cases where collection chamber 138 is multi-use and requires sterilization As shown in FIG. 1, apparatus 100 may include handpiece 140. The shape of handpiece 140 as shown in the embodiment of FIG. 1 may allow for the user to grip and manipulate the apparatus in a number of different ways. For example, the user may grasp handpiece 140 using an overhand "screwdriver" grip. This grip may be beneficial for coarse movements such as insertion. In another example, the user may employ a "pencil" grip. This grip may be beneficial for fine or delicate movements, such as the navigation of apparatus 100 to the appropriate tissue. These techniques for gripping handpiece 140 are given as examples only, and are not meant to limit the manner in which the user may grip the handpiece. In one embodiment, a switch 142 may be recessed radially on handpiece 140, as shown in FIG. 1, thereby helping to prevent apparatus 100 from being inadvertently engaged. In another embodiment, handpiece 140 may comprise a latch or guard to prevent switch 142 from being inadvertently engaged.

Handpiece 140 may generally be sized to accommodate a number of hand sizes. In a specific embodiment, handpiece 140 may be structured to allow a user to easily grasp and manipulate the apparatus.

The internal structure of one embodiment of handpiece 140 is shown in FIG. 5. In such an embodiment, handpiece 140 may be structured to house a battery 502, a motor 500, and electrical connections 110 therebetween. In addition, switch 142 may be located on handpiece 140, thereby rendering apparatus 100 self contained and/or wireless. In this embodiment, handpiece 140 may include an opening 504 for proximal end 130 of shaft 128 to enter handpiece 140. Alternatively, in an embodiment where the shaft does not enter handpiece 140, handpiece 140 may include an aperture for the electrical connections joining the motor to the shaft to exit therethrough. In one embodiment, the distalmost portion of handpiece 140 may connected to proximal end 106 of elongate member 102. This connection may be temporary via a luer lock, a snap fit, or any other type of anchoring, or may be permanent via the use of adhesives. The connection may allow shaft 128 of the tissue removal member 116 to extend therethrough. In these embodiments, handpiece 140 is preferably hollow and defines a lumen.

Handpiece 140 may be manufactured from a number of different materials, including, but not limited to, molded plastics. In one embodiment handpiece 140 may be formed from two pieces of molded material that are sealed together with an adhesive or other appropriate sealing technique. This would allow for motor 500, battery 502, or any other desired items to be contained within the handpiece.

In some embodiments, tissue removal member 116 may be operatively connected to a source of motorized rotational energy, for example a motor 500, to allow for rotation of tissue removal member 116. Proximal end 118 of tissue removal member 116 may be operatively connected to motor 500 by any one or more of a variety of means for connecting, including but not limited to, flexible tubing, a ball bearing joint, and a spring. The means for connecting may be flexible such that tissue removal member 116 may pivot with respect to motor 500. In one specific embodiment, motor 500 may be connected to battery 502 via standard electrical connections 110; however motor 500 may use an alternative source of power, such as a plug or cable for connecting directly to a power outlet or other power supply. Switch 142 is under the control of the user and allows current to flow from the source of power to motor 500 when switch 142 in engaged. When switch 142 is engaged, motor 500 may cause shaft 128 of tissue removal member 116 to rotate, thereby rotating outwardly extending projections 126 and conveying tissue from the distal portion 122 of tissue removal member 116 to proximal portion 118. Motor 500 may be one of several types of motors including, but not limited to, a direct current motor, an alternating current motor, an air driven motor, or a piezoelectric motor. Battery 502 may be disposable or rechargeable, and may further be one of several types of battery including, but not limited to, alkaline, nickel-cadmium, or lithium. Switch 142 may be one of several types of switches including, but not limited to, a toggle, a button, a rocker, a single throw switch, or a double throw switch. Furthermore, switch 142 may be configured such that the user must hold the switch in the 'on' position for the motor to remain engaged.

In one embodiment, motor 500 may be configured to rotate over a range of speeds rather than being limited to an 'on' or 'off' position. In this embodiment, switch 142 may be configured to permit adjustment of the speed by the user. The speed may generally range from about 200 to about 15,000 rotations per minute (RPM). Alternatively, the motor may include gears to adjust the torque or speed of rotation of the shaft. In a further embodiment, motor 500 and switch 142 may be configured to allow tissue removal member 116 to rotate in an opposite direction. This may facilitate removal of tissue from apparatus 100.

In embodiments comprising a bent sheath, as described hereinabove, apparatus 100 may be modified to accommodate the bent sheath. In one embodiment, helical projections 126 may be absent over the portion of shaft 128 that is within the bend. In another embodiment, segments of shaft 128 may be absent at regions within the bend. In another embodiment, the diameters of the shaft or helical projections or both the shaft and helical projections may be reduced within the region of the bend with respect to the diameter of the sheath. In another embodiment, the thickness of helical projections 126 may be variable over the length of shaft 128. In another embodiment, the finish on the interior surface of sheath 102 may be modified to reduce any friction that may occur between sheath 102 and tissue removal member 116. In another embodiment, the speed of rotation of the shaft may be slowed, by using a geared motor, for example, in order to reduce any friction that may occur between sheath 102 and tissue removal member 116.

In some embodiments, apparatus 100 may comprise an introducer apparatus that will aid in introducing elongate member 102 into the target tissue. The introducer apparatus may include a hollow elongate introducer or cannula and an obturator. Cannula 700 may be substantially stiff or rigid, such that it may assist in piercing skin or other body tissues, or such that it may provide support for apparatus 100. Obturator 801 may be structured to cooperatively engage with cannula 700. In other words, obturator 801 may be sized to fit within the lumen of cannula 700 and may comprise means for securing obturator 801 to cannula 700. In one embodiment, the outer diameter of obturator 801 may be such that when obturator 801 is fully disposed within cannula 700, obturator 801 sufficiently fills the lumen such that tissue is prevented from entering the lumen when the introducer device is inserted into the body. In some embodiments the distal tip of obturator 801 may be sharp. In these embodiments, the distal tip of obturator 801 may be conical, beveled, or more specifically, tri-beveled. The lengths of obturator 801 and cannula 700 may vary depending on the application. In one embodiment, cannula 700 will be sized such that distal end 702 can reach the target tissue within the body while the proximal end remains outside of the body. More specifically, cannula 700 may be between about 5.5 and about 7.5 inches in length, and obturator 801 may be between about 5.5 and about 7.5 inches in length. When the target tissue is an intervertebral disc, cannula 700 may be about 6.4 inches in length, and obturator 801 may be about 6.6 inches in length. Obturator 801 may be slightly longer than the cannula 700, so that distal end 810 of the obturator may protrude from cannula 700 when fully disposed. The lumen of cannula 700 may be sized to accommodate the diameter of elongate member 102 and obturator 801, while remaining as small as possible in order to limit the invasiveness of the procedure. In a specific embodiment, the proximal regions of cannula 700 and obturator 801 are structured to be locked together with hub or lock 808. In other words, the hub or lock comprises means for securing cannula 700 to obturator 801.

In one embodiment, cannula 700 and obturator 801 may be made from a stainless steel. In other embodiments, cannula 700, obturator 801, or both may be made from other materials, such as nickel-titanium alloys for example.

As previously mentioned, elongate member 102 may be inserted through the lumen of cannula 700 in order to reach the target tissue. In such an embodiment, elongate member 102 may comprise a marking 812 on proximal portion 104, such that when distal end 110 of elongate member 102 and distal end 702 of cannula 700 are aligned, the marking will be aligned with the proximal end of cannula 700. The marking may take the form of a colored band, a dot, or a notch, for example. The use of the marking is discussed further hereinbelow.

In one embodiment, the length of cannula 700 may comprise depth markings to aid the user in the placement of introducer apparatus. Such markings would be spaced at specific distances along the length of cannula 700, for example at every inch. Such depth markings may be colored bands, notches, or dots for example.

In one embodiment, cannula 700 includes a radiopaque marker 704 for visualizing the location of the cannula with respect to the target tissue using x-ray fluoroscopic imaging. In such an embodiment, radiopaque marker 704 may be located on the distal portion of cannula 700. In another embodiment, a radiopaque marker may be included on distal tip 810 of obturator 801. Examples of such markers are disclosed in U.S. patent applications US2005000079318 (publication number US20050159797A1), and US2003000382836 (publication number US20040176759A1), both of which are incorporated herein by reference.

In another embodiment, the distal portion of cannula 700 may have one of a variety of configurations, including, but not limited to, straight, bent, or beveled. In one specific embodiment, cannula 700 is straight, while distal portion 108 of elongate member 102 is curved. In such an embodiment elongate member 102 may flexibly conform to the shape of cannula 700 while disposed within the introducer, but as it is passed through distal end 702 of cannula 100 it may reform to its curved shape.

In another embodiment, cannula 700 may include a port such that a liquid may be delivered to the target tissue via cannula 700. Such a port may be located on the proximal region of the cannula, and may comprise a hub for joining a supply of liquid thereto.

As persons of skill in the art will recognize, the introducer device described hereinabove may be used with other devices that are structured to remove tissue from a nucleus pulposus. The use of the introducer device is therefore not limited to use with apparatus 100.

In a further embodiment, apparatus 100 may be operable to deliver energy to a portion of the target tissue to further treat the tissue. This energy may comprise radiofrequency electrical energy, thermal energy, microwave energy, ultrasound energy, or optical energy (e.g. laser energy). In a further embodiment, apparatus 100 may further comprise a probe operable to deliver energy, wherein probe refers to any element designed to deliver energy to a tissue. In the case of a herniated intervertebral disc, the application of radio frequency energy may cause the heating of the tissue surrounding the probe. This may result in the shrinkage of the nucleus pulposus tissue, which may act to further treat the herniated disc. Examples of the use of energy to treat an intervertebral disc are disclosed in U.S. Pat. No. 6,896,675 (filed on 5 Mar. 2002) and U.S. patent application publication number US20050234445A1, incorporated herein by reference.

In another embodiment, apparatus 100 may comprise means for measuring pressure within a patient's body. Examples of means for measuring pressure are a pressure transducer, or a fluid filled lumen for transmitting pressure. For example, in the case of an intervertebral disc, there is an intrinsic pressure associated with the nucleus pulposus tissue, and the pressure may be heightened in the case of a diseased disc. The initial pressure, change in pressure, or final pressure may be used to determine the amount of tissue to be removed from the disc. In this embodiment, a pressure sensor may be located in distal portion 108 of elongate member 102 or distal portion 134 of shaft 128, or alternatively, on a separate instrument introduced into the target tissue. Furthermore, electronic circuitry may be provided to cause an auto-shutoff of apparatus 100 when a certain pressure has been reached.

In another embodiment, apparatus 100 may comprise means for measuring the electrical impedance within a patient's body. This feature may be useful, for example, in ensuring the proper placement of apparatus 100 in the target tissue. In the case of an intervertebral disc, the impedance within the annulus fibrosis of an intervertebral disc may be different from that within the nucleus pulposus of the disc. Thus, by measuring the impedance between distal end 110 of elongate member 102 and a return electrode, for example, it may be possible to determine whether distal end 110 of elongate member 102 is in the annulus fibrosis or nucleus pulposus. The impedance may be measured between a variety of elements on the apparatus, for example between elongate member 102 and a return electrode, elongate member 102 and tissue removal member 116, tissue removal member 116 and a return electrode, obturator 801 and a grounding pad, or between any other desired elements of the apparatus.

In another embodiment, apparatus 100 may comprise sensing means for indicating whether tissue removal member 116 is contacting or engaging tissue. Such means may include, but are not limited to, an element for measuring the torque required to turn motor 500, an element for measuring the forces exerted on elongate member 102, or an element for measuring the current drawn by motor 500. The sensing means may be coupled to an indicator, such as a light or an LED, for indicating to the user that the tissue has been engaged.

In some embodiments, apparatus 100 may comprise means for guiding distal end 110 of elongate member 102 in a desired direction. For example, a pull-wire may be coupled to distal end 110 of elongate member 102, and may extend proximally to a point located outside of the patient's body. By pulling on the pull-wire, the user may cause distal end 110 of elongate member 102 to deflect to a location that is closer to a target site.

In yet another embodiment, apparatus 100 may comprise an observation system for visualizing the location or operation of apparatus 100. Such a system may include, but is not limited to, an ultrasonic or fiber-optic visualization apparatus disposed at distal end 110 of elongate member 102 or tissue removal member 116. Apparatus 100 may alternatively be configured for use with an endoscope.

In another embodiment, apparatus 100 may comprise measuring means for measuring the temperature at a particular position on the apparatus. Such means may include a thermocouple, thermistor, or resistance thermometer, for example. The temperature measurement means may be located on distal end 110 of sheath 102, or distal end 136 of shaft 128 for example.

Method

In one broad aspect, the invention comprises methods for removal of tissue from a body, wherein the methods are a combination of coring and conveyance. The methods described herein may be used to remove various types of materials from a patient's body. Examples of such materials include, but are not limited to, tissue of an intervertebral disc (for example, the nucleus pulposus), tumor tissue (including, but not limited to, material from breast, colon, stomach, or liver tumors), bone tissue (for example, bone marrow), cyst material, adipose tissue, eye material, cartilage, or atherosclerotic material.

While the general method for removing material may substantially comprise similar steps (i.e. coring and conveyance of material) regardless of the material being removed, the method of introducing the apparatus into, or removing the apparatus from, the target site, may vary depending on the material and/or target site. For example, in the case of bone marrow an instrument for penetrating bone, for example a hammer or a reamer, may be used to access the portion of the bone where the marrow is located. In the case of tumor material, extra caution may be required to ensure that malignant cells do not track along the removal path of the sheath of the tissue removal member so that tumor material is not spread within the patient's body. In such an application, it may be useful to cauterize the removal path of the sheath so that tissue surrounding the path is destroyed. If a cannula is used to introduce the device and remains in place during the procedure, as discussed herein below, the cauterization step may not be necessary, since the sheath of the tissue removal member doesn't contact tissue as it's removed from the patient's body.

In one embodiment, the method of the present invention may be practiced using apparatus 100, including tissue removal member 116 disposed within elongate member 102, as described hereinabove. Alternatively, embodiments of the method of the present invention may be practiced using any device that provides substantially similar functionality with respect to the steps of coring and conveying material. The steps of one embodiment of the method may be described generally as follows: patient preparation, insertion of the apparatus, activation of the apparatus, removal of the apparatus and patient recovery. In addition, a user may desire to analyze the tissue removed during the procedure. These steps will presently be discussed in greater detail. In order to illustrate the steps of this embodiment, reference will be made to a specific application of this embodiment in removal of tissue from an intervertebral disc (shown in FIGS. 8A-8L). It should be noted that the steps described herein are not intended to be exclusive and further steps may be performed in conjunction with embodiments of the method of the present invention. In addition, some of the steps described herein may be omitted and the invention is not limited in this regard.

The step of patient preparation may comprise acquiring patient data in order to prepare for the procedure as well as positioning the patient appropriately. Pertinent data to be acquired may include, but is not limited to, a medical history of the patient, standard diagnostic test results (e.g. blood tests), physical function and pain assessments and medical imaging assessments of the patient's condition. In some embodiments, the patient may be assessed using various imaging, modalities such as MRI, X-ray, CT scan or ultrasound prior to the tissue removal procedure. These assessments may aid in determining the appropriate location of the target site for tissue removal as well as the amount of tissue to be removed. Prior to commencing the procedure, the patient may be positioned in a prone position (depending on the target site and the material being removed) and prepared using standard pre-surgical techniques.

Once preparations for the procedure have been completed, the apparatus may be inserted to the target site within the patient's body. The location and angle of insertion may depend on the target site and the specific material being removed. For example, in the case of an intervertebral disc, the physician may insert the apparatus into the foraminal and pedicle zones, superior to the articular process, below the exiting spinal nerve, 200 to 400 from the sagittal plane, and roughly equidistant from the superior and inferior endplates.

Figures 8A, 8B:
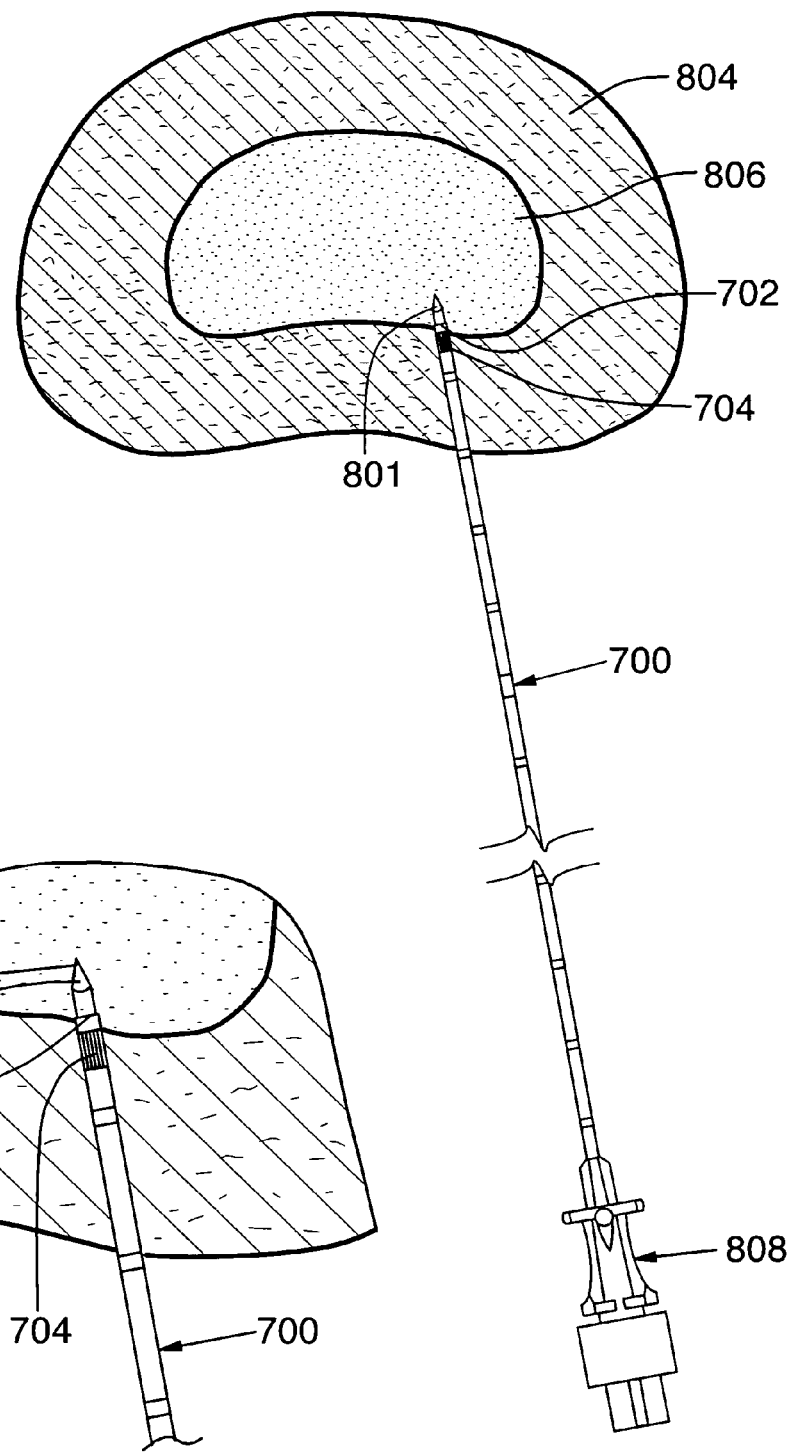
FIGS. 8A-8L are illustrations of one embodiment of an application of the method of the invention.
Figure 8D:
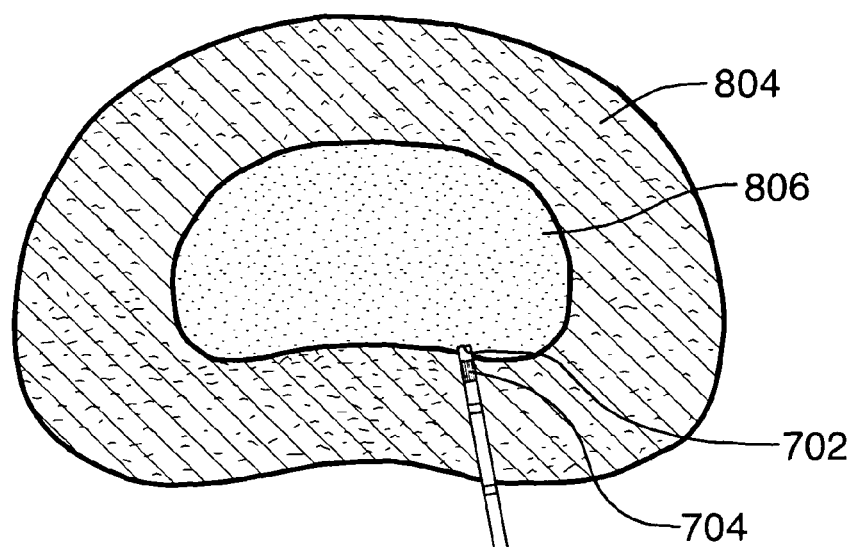
Figure 8C:
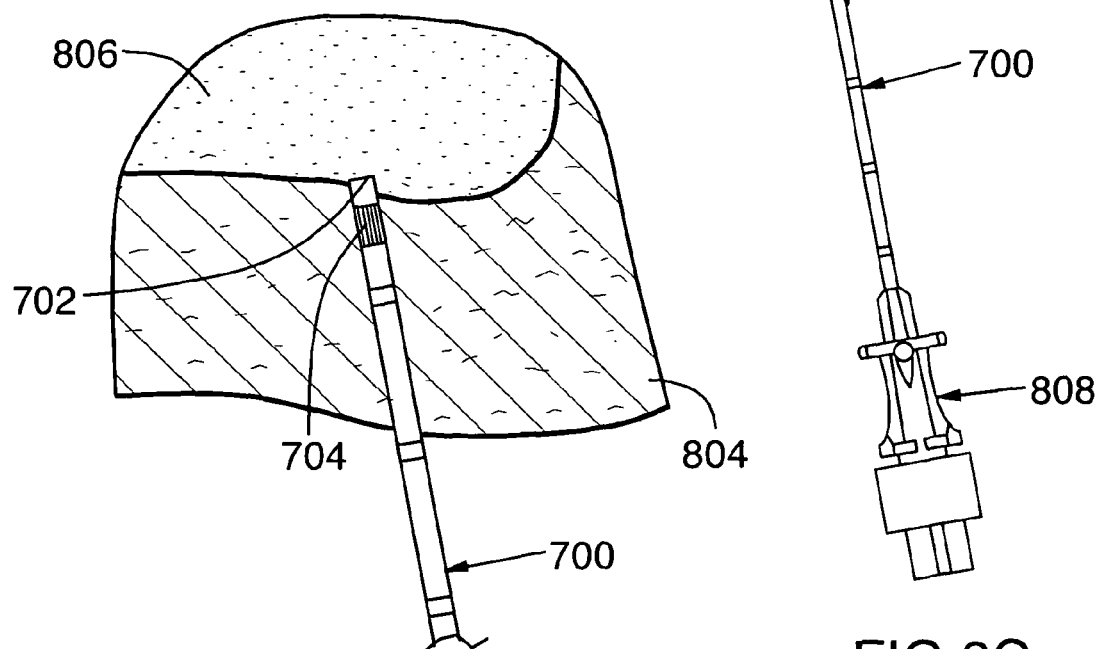

In some embodiments, the placement of distal end 110 of elongate member 102 at the target site may be aided with the use of an introducer apparatus. Referring now to the example illustrated in FIGS. 8A and 8B, the introducer apparatus comprises an obturator 801 disposed within a cannula 700. The introducer apparatus is advanced either percutaneously or in an open surgical procedure into the body of the patient and towards the target site. When the target site has been reached, obturator 801 is withdrawn proximally from cannula 700, leaving a distal end 702 of cannula 700 at the target site, for example as shown in FIGS. 8C and 8D. In the illustrated embodiment, distal end 702 of cannula 700 is positioned at the boundary between the annulus fibrosis 804 and the nucleus pulposus 806 (i.e. the inner wall of the intervertebral disc).

In some embodiments, cannula 700 may comprise a radiopaque marker 704 to aid in the placement of the introducer apparatus. In such an embodiment, radiopaque marker 704 may be included at distal end 702 of cannula 700. In alternate embodiments, radiopaque marker 704 may be located elsewhere on cannula 700. The placement of cannula 700 may then be performed under fluoroscopy, such that the visibility of distal end 702 of cannula 700 may be enhanced on the fluoroscopic image by radiopaque marker 704. Alternatively or in addition, various sensors may be used to assist in placing the introducer apparatus appropriately. For example, in the case of an intervertebral disc, an impedance measurement device may be included on distal end 702 of cannula 700. As the annulus fibrosis of an intervertebral disc may be of different electrical impedance than the nucleus pulposus, the user may measure the electrical impedance at distal end 702 of cannula 700 while inserting the cannula. When the electrical impedance measurement indicates that distal end 702 of cannula 700 has passed through the annulus fibrosis and is within the nucleus pulposus, the user may stop the insertion process. In further embodiments, a contrast solution may be injected at the target site through the lumen of cannula 700 in order to verify proper placement. For example, if the target site is located within an intervertebral disc, the contrast solution, when viewed under fluoroscopy, may allow a user to visualize the boundary between the nucleus pulposus 806 and annulus fibrosis 804. In addition, other substances may be injected through cannula 700 to the target site. The substance may be injected through an injection port or hub coupled to cannula 700. For example, it may be desirable to inject a fluid, including but not limited to an antibiotic, an anesthetic or an analgesic substance, prior to removing tissue from the target site.

Once cannula 700 is properly placed and any injections have been completed, elongate member 102 may be inserted through the lumen of cannula 700. For example, and referring now to FIGS. 8E and 8F, elongate member 102 and tissue removal member 116 may be advanced through the lumen of cannula 700, such that distal end 110 of elongate member 102 is located distal to distal end 702 of cannula 700.

The device having been inserted to the target site, the procedure may proceed by activating the tissue removal member in order to remove tissue. This step of activating the device may generally include engaging the motor to rotate the device and advancing the device, including elongate member 102, through the target site to core and convey a desired amount of material away from the target site. More specifically, in one embodiment, the user may advance distal end 110 of elongate member 102 into the target site, engage motor 500, usually via switch 142, and while motor 500 is engaged, advance apparatus 100 distally through the target site. When apparatus 100 has been advanced a particular distance, to be determined by the user depending on the size of the target site and/or the amount of material to be removed, motor 500 may be disengaged, and elongate member 102 may be withdrawn proximally through the target site. In the case of a curved elongate member, as shown in FIG. 2, elongate member 102 may be repositioned by rotating elongate member 102 about its longitudinal axis, without requiring removal and re-insertion of elongate member 102 into the patient's body. Motor 500 may then be re-engaged, and elongate member 102 may be advanced into a second region of the target site. The activation step of the tissue removal procedure may be repeated until the desired volume of tissue has been removed. At this point, apparatus 100 may be removed from the body, as discussed further below. It should be noted that, in some embodiments, only one pass of elongate member 102 may be required in order to remove the desired amount of tissue.

Without being restricted to a specific theory of operation, a proposed mechanism of action of apparatus 100, in one embodiment of the present invention, will be presently described. In operation, tissue removal member 116 remains substantially static or stationary with respect to the longitudinal axis of elongate member 102. In other words, tissue removal member 116 does not move 'in and out' with respect to elongate member 102. Apparatus 100 is advanced through the target site to core the material to be removed. As apparatus 100 is advanced, material enters elongate member 102 through aperture 112 and is forced proximally into elongate member 102 by the advancement of apparatus 100. In other words, material is substantially gathered into the lumen of elongate member 102. As used herein, the term "substantially gathered" may refer to a sample or portion of tissue that is still connected with tissue outside of the lumen of elongate member 102, or may alternatively refer to tissue that has been detached from tissue outside of the lumen. At a certain location within elongate member 102, the material contacts tissue removal member 116, which functions to convey the material proximally from distal portion 108 of elongate member 102, to, for example, the exterior of the patient's body. Tissue removal member 116 may function by a variety of mechanisms. In one embodiment, tissue removal member 116 is coupled to motor 500. Upon engagement of motor 500, tissue removal member 116 rotates about its longitudinal axis. Outwardly extending projections 126, described hereinabove, will engage the tissue within elongate member 102, and convey the tissue toward proximal end 120 of tissue removal member 116. In one specific embodiment, proximal portion 118 of tissue removal member 116 is operatively connected to collection chamber 138 as described hereinabove. In this embodiment, the tissue may be conveyed from distal portion 108 of elongate member 102 and be deposited within chamber 138. As described hereinabove, tissue removal member 116 is recessed from distal tip 110 of elongate member 102; therefore the material does not contact tissue removal member 116 until after the material has entered the lumen of elongate member 102. This functions to protect any non-target tissue from tissue removal member 116. For example, in the case of an intervertebral disc, as shown in FIGS. 8I to 8L, apparatus 100 is advanced through the soft tissue of nucleus pulposus 806 to effect removal of the tissue as described above. As apparatus 100 is advanced, it may eventually contact annulus fibrosis 804, the integrity of which is essential to the health of the disc. Due to the more rigid structure of the annulus fibrosis, it may be prevented from being cored into elongate member 102, and therefore, due to the fact that tissue removal member 116 is recessed from distal tip 110, the annulus fibrosis will not contact tissue removal member 116. Thus, the annulus fibrosis may be protected from the high speed motion and projections of tissue removal member 116.

Figures 8G, 8H:
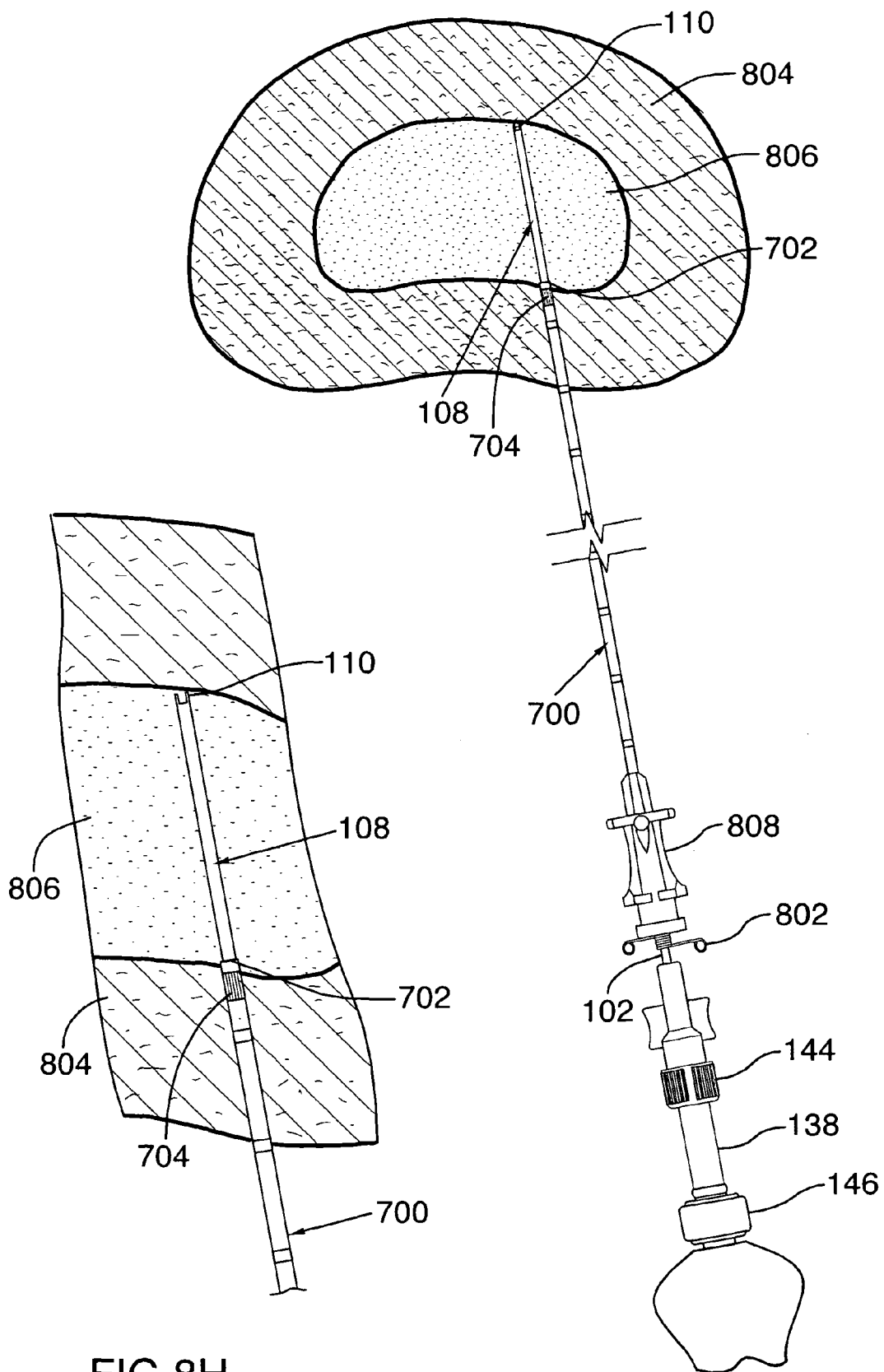
Figure 8:
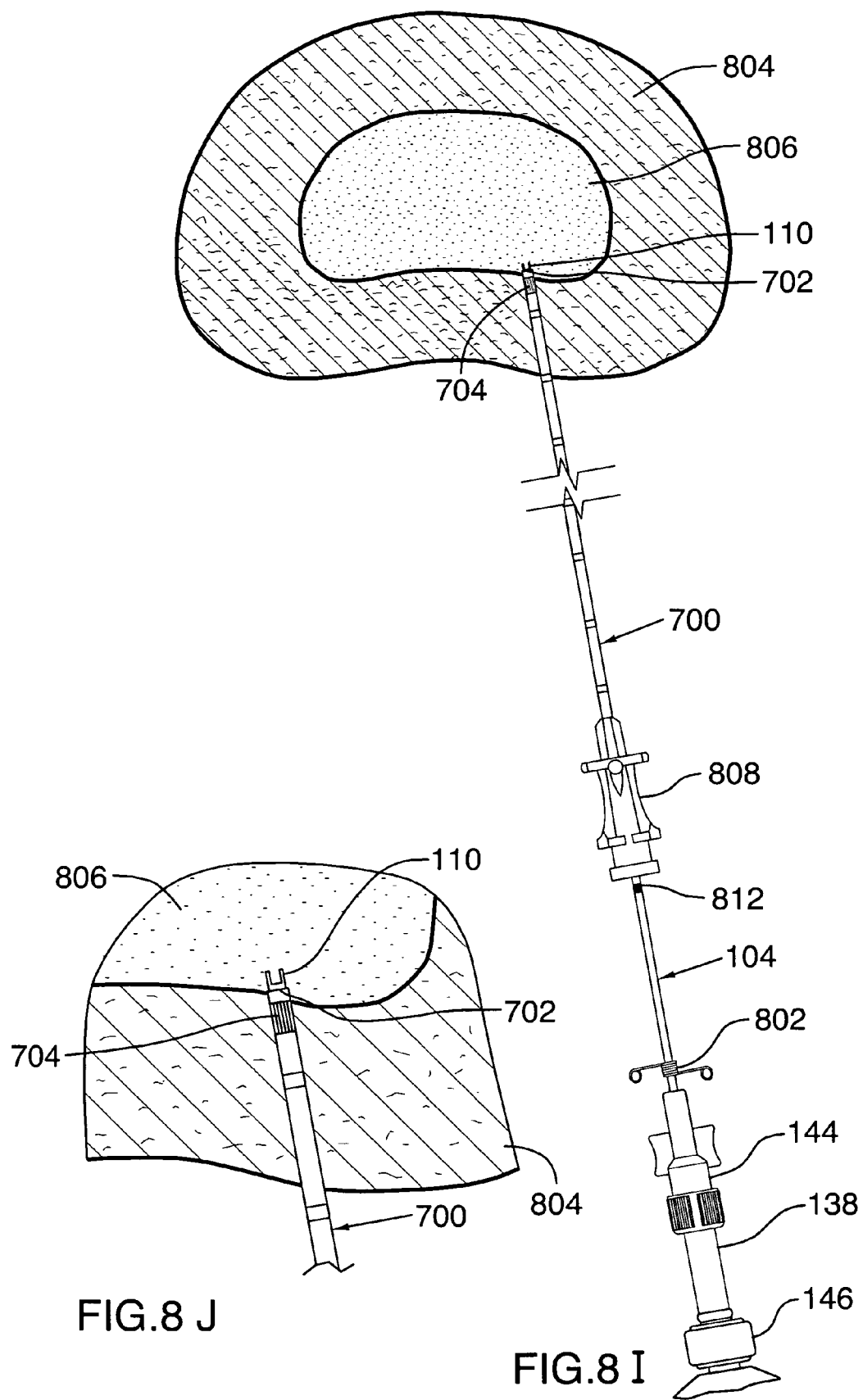
Figures 8K, 8L:
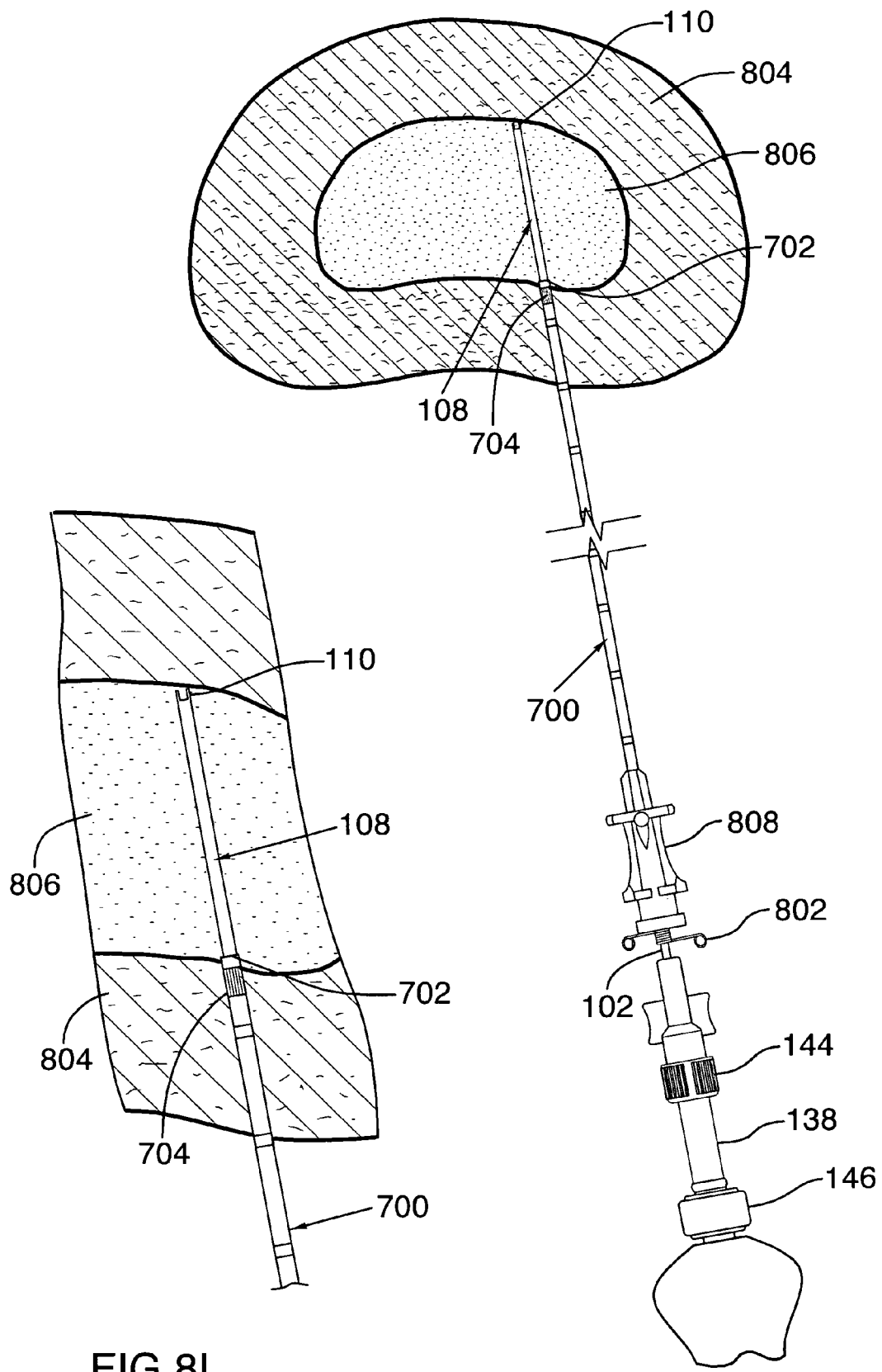

In some embodiments, for example as shown in FIGS. 8G to 8L, a clip 802, sliding depth marker, or other marking mechanism may be used to indicate the location of distal end 110 of elongate member 102 within the patient's body. For example, in the case of an intervertebral disc, the user may position distal end 110 of elongate member 102 at the boundary of annulus fibrosis 804 and nucleus pulposus 806, as described above with respect to the positioning step. As shown in FIGS. 8G and 8H, the user may then advance elongate member 102 distally through nucleus pulposus 806, without activating tissue removal member 116, until distal end 110 of elongate member 102 contacts annulus fibrosis 804 on the anterior side or portion of the disc. This point of contact may be referred to the as the "anterior annulus inner wall" of the intervertebral disc. The boundary between nucleus pulposus 806 and annulus fibrosis 804 may be located by tactile sensation, as the annulus fibrosis 804 is generally stiffer than the nucleus pulposus 806, or by using a contrast solution and performing the method under fluoroscopy, as described hereinabove. The user may place marker or clip 802 on the distalmost portion of elongate member 102 that is proximal to the proximal end of cannula 700, as shown in FIG. 8G. Referring now to FIGS. 8I and 8J, the user may then retract distal end 110 of elongate member 102 proximally to distal end 702 of cannula 700. In one embodiment, proximal portion 104 of elongate member 102 may comprise a marking 812 located such that when the marking is aligned with the proximal end of cannula 700, it indicates that the distal ends of cannula 700 and elongate member 102 are aligned. Thus, when elongate member 102 is withdrawn proximally through the disc, the user will know to stop retracting elongate member 102 when marking 812 is aligned with the proximal end of cannula 700. The user may then engage tissue removal member 116, and begin the coring and conveyance procedure. As shown in FIGS. 8K and 8L, the user may stop advancing apparatus 100 through the disc as marker or clip 802 approaches the proximal end of cannula 700. The user may then withdraw apparatus 100 by realigning the marking with the proximal end of cannula 700, and repeat the coring and conveying step. The use of marker or clip 802 may help to ensure that distal end 110 of elongate member 102 does not contact annulus fibrosis 804. This may be especially advantageous in the case of a severely damaged disc that may be severely affected by damage to annulus fibrosis 804.

Termination of the procedure may be decided by a user, which decision may be facilitated in one or more ways by the apparatus being used. For example, the procedure may be terminated once a sufficient amount of tissue has been removed. In the case of an intervertebral disc, the amount of tissue to be removed may be up to 3.0 grams, more specifically, between 0.05 and 1.5 grams. Several methods may be used to determine when the appropriate amount of tissue has been removed from the body. In one embodiment, collection chamber 138 is at least partially pervious to light and comprises volume markings for determining the amount of tissue held within chamber 138. By visualizing the markings and/or the contents of collection chamber 138, the user may decide when the desired amount of tissue has been removed. Alternatively, collection chamber 138 may comprise a sensing means for automatically indicating when a desired amount of tissue has been removed. For example, collection chamber 138 may be fitted with a sensor, including but not limited to a pressure, optical or chemical sensor, such that the sensor may provide an indication to the user once a desired amount of tissue has been collected. The sensor may be movable so that the user can adjust for the desired amount of tissue for a given procedure. In one embodiment, tissue may be collected and, once the amount of tissue collected is such that the tissue contacts the sensor, the sensor may provide an indication, for example, a visible or audible indication, that the desired amount of tissue has been removed.

In another embodiment, a pressure monitoring device may be coupled to apparatus 100. By monitoring the change in pressure at the target site, the user may determine when the desired amount of tissue has been removed. Alternatively, the pressure monitoring device may be operable to provide an indication to the user when the pressure has changed by a pre-determined amount. The indication may take the form of, for example, a visible or audible indication and may indicate to the user that the desired amount of tissue has been removed. These embodiments are meant to be exemplary only, and are not intended to limit the methods for determining when the appropriate amount of tissue has been removed.

Once the procedure has been terminated, the tissue removal member, as well as other components of the apparatus being used, may be removed from the patient's body. The step of removing these components may include, in some embodiments, removing elongate member 102 from cannula 700, injecting a substance through cannula 700 and removing cannula 700 from the patient's body. For example, it may be beneficial to inject a fluid, including but not limited to an antibiotic fluid, into the target site to prevent the possibility of infection.

In some embodiments, apparatus 100 may be maneuvered by the user during, for example, the positioning, advancing, and removing steps, by grasping handpiece 140 in one or more of a variety of grips, as described hereinabove, and manipulating handpiece 140 to control the position of elongate member 102 and tissue removal member 116 at the target site.

The entire treatment procedure described herein may be repeated at a different site, if necessary. Following completion of all such procedures, the patient should be allowed to recover. In addition, the user may collect material removed from the patient during the procedure in order to allow for further analysis. Collecting material from the tissue removal member may be accomplished in several ways. For example, material may be removed from tissue removal member 116 manually by scraping, tweezing or otherwise grasping and removing the material. Alternatively, if material has been collected within collection chamber 138, then chamber 138 may be removed from apparatus 100, sealed and/or capped and sent for analysis. In addition, as described further below, motor 500 may be run at high speeds in order to convey material up to collection chamber 138 prior to removal of chamber 138. Furthermore, motor 500 may be operable to run in reverse, such that material may be conveyed to distal portion 122 of tissue removal member 116 which may allow for easier removal of material from apparatus 100, for example.

In another embodiment, apparatus 100 may be used to introduce material into a patient's body. For example, in the case of an intervertebral disc, it may be desired to add artificial (for example, synthetic) or natural (for example, xenobiotic) material or tissue, such as collagen or cement, into the intervertebral disc. In this embodiment, the material may be housed in receptacle 138, and motor 500 may be run in the reverse direction from that used in the tissue removal process. In this embodiment, tissue removal member 116 may be referred to as a motorized device. The motorized device may engage the material housed in the receptacle, and convey it distally through the lumen of elongate element 102 and deposit it in the body. In one specific embodiment, tissue may be removed from the patient's body, and then material may be introduced into the patient's body. In this embodiment, after the tissue has been removed from the body as described above, apparatus 100 may be removed from the body and introducer apparatus, and the receptacle housing the tissue may be replaced with a receptacle housing the material to be introduced. Device 100 may then be re-introduced into the patient's body, as described hereinabove, and the motor may be run in reverse to convey the material into the body. Device 100 may be advanced and withdrawn within the target tissue in order to disperse the material. In another embodiment, material may be introduced to the target site prior to removal of tissue from the patient's body. In yet another embodiment, material other than tissue, referred to herein as a "second material", such as previously introduced cements or pharmaceutical compounds, may be removed from the target site. This may be done either before or after the introduction of material, and before or after a step of removing tissue.

Some embodiments of the method aspect of the present invention may comprise one or more further steps. For example, in one embodiment, the method may comprise a step of delivering energy to the target site before, during, or after removal of material. In this embodiment, apparatus 100 may include a probe or other device capable of delivering energy, as described hereinabove. The method may thus include placement of the probe at the target site, and activation of the probe to deliver energy. The user may advance or otherwise move the probe within the tissue, or may keep the probe stationary. Further details regarding such an embodiment may be found in co-pending U.S. patent application 20050234445 (published on 20 Oct. 2005), incorporated herein by reference.

In another embodiment, a second device may be separately introduced into the patient's body. This device may be used to aid in the collection of material. For example, as elongate member 102 and tissue removal member 116 are being operated at the target site, the secondary device may be used to push tissue towards elongate member 102.

In yet another embodiment, the method further comprises a step of disposing of apparatus 100 after use. This may be beneficial as single-use devices avoid several problems associated with reusable devices, including those associated with bacterial infections, viruses, and prions.

In some embodiments, the method may comprise one or more steps of variably adjusting the speed (i.e. rotations per minute—RPM) of motor 500. In such embodiments, motor 500 is capable of rotating at various speeds, and the speed of motor 500 may be adjusted by the user. For example, the user may adjust the speed by using a control element such as a dial, lever, knob, or any other control element coupled to motor 500. In one such embodiment, a user may adjust the motor to run at a high speed as the user begins the tissue removal procedure, wherein a high speed may be desirable to assist in rapidly removing material. Towards the end of the procedure, however, the user may reduce the speed to ensure that an excess of tissue is not removed. Furthermore, when the procedure is completed and apparatus 100 has been removed from the patient's body, the user may desire to rotate tissue removal member 116 at a high speed to remove any tissue remaining in elongate member 102 or on tissue removal member 116.

In another embodiment, the longitudinal motion of apparatus 100 may be automated. In such an embodiment, the advancement of apparatus 100 into and through the target site would be automatic, rather than as a result of force applied by the user.

As mentioned above, this embodiment of the method of the present invention is not intended to be limited to use within an intervertebral disc. Other tissues and/or materials may be removed from a patient's body using the steps described above. Embodiments of the present invention thus provide for a minimally invasive apparatus that may be used to remove material, for example tissue from a patient's body, while minimizing blood loss and trauma to the patient.

The embodiments of the invention described above are intended to be exemplary only. The scope of the invention is therefore intended to be limited solely by the scope of the appended claims.

It is appreciated that certain features of the invention, which are, for clarity, described in the context of separate embodiments, may also be provided in combination in a single embodiment. Conversely, various features of the invention, which are, for brevity, described in the context of a single embodiment, may also be provided separately or in any suitable sub-combination.

Although the invention has been described in conjunction with specific embodiments thereof, it is evident that many alternatives, modifications and variations will be apparent to those skilled in the art. Accordingly, it is intended to embrace all such alternatives, modifications and variations that fall within the spirit and broad scope of the appended claims. All publications, patents and patent applications mentioned in this specification are herein incorporated in their entirety by reference into the specification, to the same extent as if each individual publication, patent or patent application was specifically and individually indicated to be incorporated herein by reference. In addition, citation or identification of any reference in this application shall not be construed as an admission that such reference is available as prior art to the present invention.

We claim:

1. A method for introducing material into a region of a patient's body, comprising the steps of:
    providing an elongate member for introducing said material, said elongate member defining a lumen and comprising a distal end defining an aperture and a proximal end;
    positioning the elongate member at a target side of a patient's body;
    providing a motorized device at least partially disposed within said lumen, the motorized device including a shaft and helical projections extending from the shaft; and
    introducing the material through said lumen into said target site by rotating the shaft of said motorized device within the lumen, the helical projections moving the material toward the distal end and out the aperture, wherein said material is selected from the group consisting of synthetic tissues and cements.

2. The method of claim 1, wherein said motorized device remains substantially static with respect to a longitudinal axis of said elongate member during the step of introducing material.

3. The method of claim 1, further comprising a step of positioning said elongate member at said target site of said patient's body.

4. The method of claim 3, wherein said step of positioning said elongate member is facilitated by fluoroscopic visualization.

5. The method of claim 3, wherein said step of positioning said elongate member further comprises the steps of:
    providing an introducer apparatus comprising a cannula defining a cannula lumen and an obturator disposed within said cannula lumen;

inserting said introducer apparatus into said patient's body such that a distal end of said cannula is positioned at said target site of said patient's body;

withdrawing said obturator from said cannula lumen; and inserting said elongate member into said cannula lumen.

6. The method of claim 5, wherein said step of inserting said introducer apparatus in facilitated by fluoroscopic visualization.

7. The method of claim 5, further comprising a step of injecting a fluid through said cannula lumen.

8. The method of claim 7 wherein said fluid is selected from the group consisting of an anesthetic, an antibiotic and a dye.

9. The method of claim 5, wherein said distal end of said cannula is positioned at a posterior portion of a nucleus pulposus of an intervertebral disc of said patient's body.

10. The method of claim 1, further comprising a step of removing at least one of the material, a second material and tissue from said target site.

11. The method of claim 10, wherein said tissue is tissue of a nucleus pulposus of an intervertebral disc.

12. The method of claim 1, wherein a distal end of said motorized device is spaced from said aperture in a direction toward the proximal end of the lumen when the motorized device is fully disposed within the elongate member, wherein the location of said distal end of said motorized device functions to reduce the likelihood of damage to non-target tissue.

13. The method of claim 1, wherein at least one of said elongate member and said motorized device are operatively connected to a handpiece and wherein a motor is housed within said handpiece and is operatively connected to said motorized device.

14. The method of claim 1, wherein said motorized device comprises an auger.

15. The method of claim 14, wherein said motor is capable of rotating said auger in a forward or a reverse direction.

16. The method of claim 1, wherein a distal portion of said elongate member defines at least one slot extending proximally from a distal end of said elongate member.

17. The method of claim 1, wherein a proximal end of said elongate member is operatively connected to a receptacle structured to house said material.

18. The method of claim 17, wherein said receptacle is at least partially pervious to light.

* * * * *

UNITED STATES PATENT AND TRADEMARK OFFICE
CERTIFICATE OF CORRECTION

| | |
|---|---|
| PATENT NO. | : 8,201,563 B2 |
| APPLICATION NO. | : 11/368508 |
| DATED | : June 19, 2012 |
| INVENTOR(S) | : Conquergood et al. |

It is certified that error appears in the above-identified patent and that said Letters Patent is hereby corrected as shown below:

On the Title page:

Item (56) References Cited under U.S. Patent Documents on Page 2, 2nd column last item, please delete "6,733,492 B2  5/2004  Ashley et al."

and replace with "6,733,496 B2  5/2004  Sharkey et al."

Signed and Sealed this
Fourth Day of September, 2012

David J. Kappos
*Director of the United States Patent and Trademark Office*